United States Patent
Brevet et al.

(10) Patent No.: US 8,425,879 B2
(45) Date of Patent: Apr. 23, 2013

(54) METALLOPORPHYRIN DERIVATIVES, NANOPARTICLES COMPRISING THE SAME, AND USE THEREOF FOR PHOTODYNAMIC THERAPY

(75) Inventors: David Brevet, Montpellier (FR); Ouahiba Hocine, Tizi Ouzou (DZ); Jean-Olivier Durand, Palavas-les-Flots (FR); Philippe Maillard, Saint Cyr l'école (FR); Alain Morere, Les Matelles (FR); Marcel Garcia, Prades-le-Lez (FR); Monique Smaïhi, Castelnan le Lez (FR); Magali Gary-Bobo, Montpellier (FR)

(73) Assignees: Centre National de la Recherche Scientifique, Paris (FR); Institut Curie, Paris Cedex 05 (FR); Universite Mouloud Mammeri, Tizi Ouzou (DZ); Universite Montpellier 2, Montpellier (FR)

( * ) Notice: Subject to any disclaimer, the term of this patent is extended or adjusted under 35 U.S.C. 154(b) by 154 days.

(21) Appl. No.: 13/063,834

(22) PCT Filed: Sep. 14, 2009

(86) PCT No.: PCT/FR2009/001090
§ 371 (c)(1),
(2), (4) Date: May 4, 2011

(87) PCT Pub. No.: WO2010/029232
PCT Pub. Date: Mar. 18, 2010

(65) Prior Publication Data
US 2011/0262357 A1      Oct. 27, 2011

(30) Foreign Application Priority Data

Sep. 15, 2008   (FR) ...................... 08 05034

(51) Int. Cl.
*A61K 49/00*   (2006.01)
*A61K 9/00*    (2006.01)
*A01N 55/00*   (2006.01)
*C07B 47/00*   (2006.01)

(52) U.S. Cl.
USPC .............. 424/9.1; 424/400; 514/63; 540/145

(58) Field of Classification Search ............... 424/9.1, 424/400; 514/63; 540/145
See application file for complete search history.

(56) References Cited

FOREIGN PATENT DOCUMENTS
EP   0345171    12/1989
WO   94/09003   4/1994

OTHER PUBLICATIONS

Paolo Zucca, et al, 5,10,15,20-Tetrakis(4-sulfonatophenyl)porphine-Mn(III) immobilized on Imidazole-activated Silica as a Novel Lignin-Peroxidase-Like Biomimetic Catalyst, 278 J. Mol. Catal. A: Chem. 220 (2007).*
Dolmans, Photodynamic Therapy for Cancer, 3 Nature Rev. Cancer 380 (2003).*
Ohulchanskyy, Organically Modified Silica Nanoparticles with Covalently Incorporated Photosensitizer for Photodynamic Therapy of Cancer, 7 Nano Let. 2835 (2007).*
Ohulchanskyy, Organically Modified Silica Nanoparticles with Covalently Incorporated Photosensitizer for Photodynamic Therapy of Cancer, Nano Letters, 7, 2835-2842, 2007.
Bonnet, A New Mesoporous Hybrid Materials: Porhyrin-Doped Aerogel as a Catalyst for the Epoxidation of Oelfins, Advanced Functional Materials, 12, 39-42, 2002.

* cited by examiner

*Primary Examiner* — Sean Basquill
(74) *Attorney, Agent, or Firm* — Morgan, Lewis & Bockius LLP

(57) ABSTRACT

Nanovectors are disclosed that make it possible to simultaneously target, image, and treat cancerous cells using photodynamic therapy. Also disclosed are novel molecules (I) derived from porphyrins, silica-based nanoparticles comprising the same, and their use in photodynamic therapy.

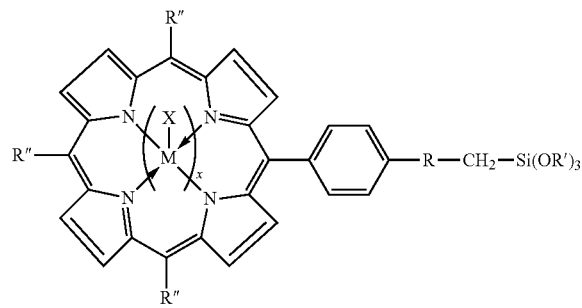

12 Claims, 14 Drawing Sheets

Pol = Polymer or carbon-based chain

= Photosensitizer

Figure 1:
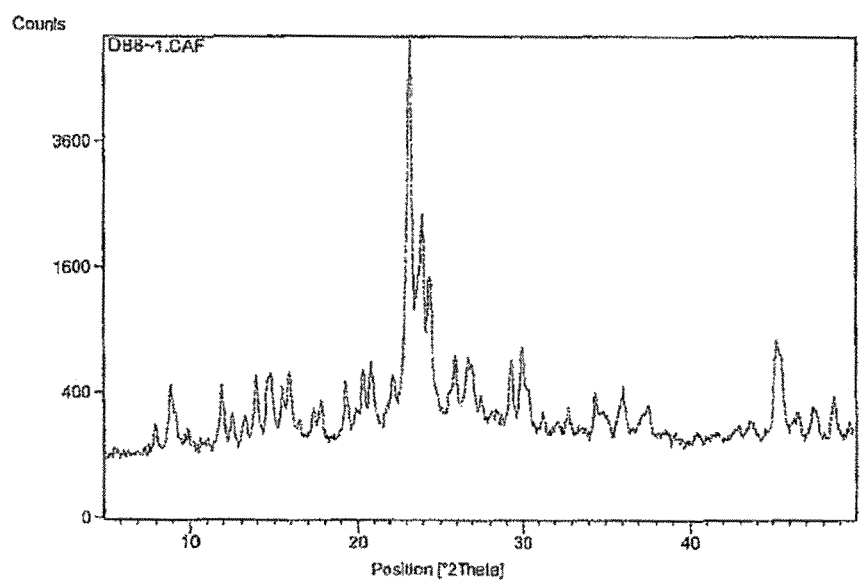

METALLOPORPHYRIN DERIVATIVES, NANOPARTICLES COMPRISING THE SAME, AND USE THEREOF FOR PHOTODYNAMIC THERAPY

RELATED APPLICATIONS

The present application is a U.S. National Phase Application of International Application No. PCT/FR2009/001090 (filed Sep. 14, 2009) which claims priority to French Patent No. 0805034 (filed Sep. 15, 2008) which are hereby incorporated by reference in their entirety.

The subject of the invention is nanovectors that make it possible to simultaneously target, image and treat, using photodynamic therapy, cancer cells. In particular, the invention is based on the use of novel molecules derived from porphyrins, siliceous nanoparticles containing same and the use thereof in photodynamic therapy.

Photodynamic therapy is based on the use of certain therapeutic molecules, called photosensitizers, which will preferentially localize in malignant tissues, and which, when they are activated using a light source of appropriate wavelength, in the visible or near infrared range, transmit their excess energy to the molecular oxygen surrounding them. This activation leads to the formation of reactive oxygen species, such as free radicals and singlet oxygen. These reactive oxygen species, and more particularly singlet oxygen, are toxic for the cells that surround them and lead to the destruction of malignant tissues in their close environment: they oxidize cell membranes and thus cause irreversible damage to the cells containing the photosensitizer. Photodynamic therapy is based on a double selectivity: firstly, selective irradiation of the tissues concerned and, secondly, relative selectivity of the photosensitizer for the target tissues. In the absence of irradiation, since the photosensitizers are not very toxic for the cells, their diffusion in the organism causes only a few drawbacks.

In order for a photosensitizer to be able to be used in vivo, it must have several qualities, and in particular it must be able to be easily delivered to cancer tissues, it must be water-soluble, easy to produce, nontoxic in the absence of irradiation, and stable with respect to circulating enzymes, it must have good tropism for tumor cells and it must be rapidly eliminated from healthy tissues. However, most of the molecules belonging to the photosensitizer category are hydrophobic and the introduction thereof into the organism, in particular parenterally, requires having recourse to particular formulations, and especially formulations in the form of colloidal suspensions, liposomes or nanoparticles. These formulations make it possible to stabilize the photosensitizers in an aqueous medium and to promote the conveyance thereof to the target tissues, in particular using specific targeting molecules. Another constraint of these formulations is that of being able to retain the effectiveness of the photosensitizers, i.e. their ability to convert the molecular oxygen which surrounds them into reactive oxygen species. This is because some formulations interact with the excited states of the photosensitizer and reduce its effectiveness.

The formulation of photosensitizers in mesoporous nanoparticles with a controlled porosity has emerged as a promising approach for application in photodynamic therapy: such formulations are described in particular in WO2004/067508; WO2008/030624; I. Roy et al., J. Am. Chem. Soc. 2003, 125, 7860-7865.

However, these formulations quite often cause premature release of the photosensitizer in the organism before said photosensitizer has reached its target.

It therefore appeared to be necessary to find means for avoiding this premature release, and one proposed solution was to develop nanoparticles to which the photosensitizer is covalently bonded.

The document T. Y. Ohulchanskyy et al., Nanolett. 2007, 2835 describes nanoformulations of a photosensitizer for photodynamic therapy, in which the photosensitizer is covalently bonded to organically modified silica nanoparticles (ORMOSIL). The photosensitizer retains its spectroscopic and functional properties, and the monodispersed nanoparticles of small size have a good affinity for cancer cells and have a high cytotoxic efficacy. The photosensitizers used are hydrophobic, which makes it necessary to carry out the synthesis in an organic medium, with solvents of which the industry today seeks to avoid large-scale use.

Document US2007/0218049 describes luminescent nanoparticles to which photosensitizers of the porphyrin family are attached. The nanoparticles described in that document are solid and nonporous, they are based on metallic molecules such as CdS, CdSe or ZnO, and the photosensitizer is grafted at the surface of these nanoparticles via a cysteine linker.

There remained therefore the need for novel nanoparticles with controlled porosity, to which photo-sensitizers are covalently bonded, in which said photo-sensitizer retains its spectroscopic and functional properties, it being possible for these nanoparticles to be prepared by simple methods which do not use toxic and/or polluting compounds.

It has been possible to prepare such nanoparticles through the development of novel photosensitizers corresponding to formula (I) below.

A first subject of the invention is therefore a molecule corresponding to formula (I) below:

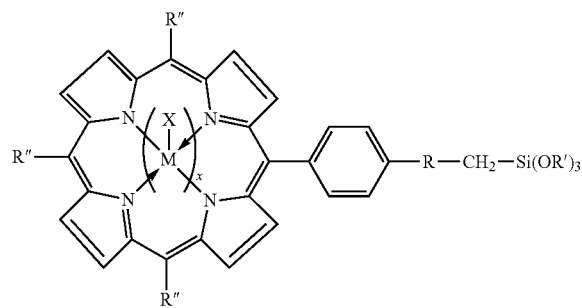

(I)

in which:

x represents an integer chosen from: 0 and 1,

M represents a metal atom chosen from transition metals, x represents a group chosen from: a halide, and an anion of a carboxylic acid which is pharmaceutically acceptable, R represents a group chosen from:

a $C_1$-$C_{15}$ alkyl chain, optionally interrupted with one or more groups chosen from: an ether (—O—), an amine (—NH—), a thioether (—S—), a ketone (—CO—), an ester (—CO—O—), an amide (—CO—NH—), a urea (—NH—CO—NH—), a thiourea (—NH—CS—NH—), an oxy-carbonyl (—O—CO—O—) and a carbamate (—NH—CO—O—), R' represents a group chosen from: a $C_1$-$C_6$ alkyl, a phenyl and a benzyl, R" represents a group chosen from:

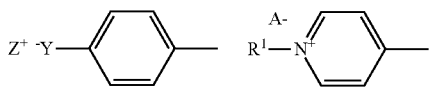

and $Z^+$ represents a pharmaceutically acceptable organic or inorganic cation,
$Y^-$ represents a group which may be chosen from: $-COO^-$ and $-SO_3^-$,
$A^-$ represents an anion which may be chosen from: a halide, and an anion of a carboxylic acid which is pharmaceutically acceptable,
$R^1$ represents a $C_1$ to $C_{10}$ alkyl.
A $C_1$-$C_{10}$ alkyl group is a linear, branched or cyclic hydrocarbon-based chain containing from 1 to 10 carbon atoms.

When x represents 0, the compound of formula (I) is a porphyrin derivative and the (M-X) groups are replaced with two hydrogen atoms.

When x represents 1, the compound of formula (I) is a metalloporphyrin derivative.

In formula (I), the variables defined above are advantageously chosen, independently, according to the following rules:

Preferably, M represents a metal atom chosen from: Zn, Pt, Pd, Mn, Gd, Ni, Cr and Ru.

Preferably, X represents a group chosen from: $Cl^-$, $Br^-$, $I^-$, acetate, propionate, butyrate, ascorbate, benzoate, cinnamate, citrate, fumarate, glycolate, malonate, tartrate, malate, maleate, mandelate and tosylate, and even more preferably: $Cl^-$, $Br^-$, $I^-$, acetate and tosylate.

Advantageously, R represents a group chosen from: a $C_1$-$C_{10}$ alkyl chain, optionally interrupted with one or more groups chosen from: an ether ($-O-$), an amine ($-NH-$), a thioether ($-S-$), a ketone ($-CO-$), an ester ($-CO-O-$), an amide ($-CO-NH-$), a urea ($-NH-CO-NH-$), a thiourea ($-NH-CS-NH-$), an oxycarbonyl ($-O-CO-O-$) and a carbamate ($-NH-CO-O-$), and, for example, R may be chosen from:

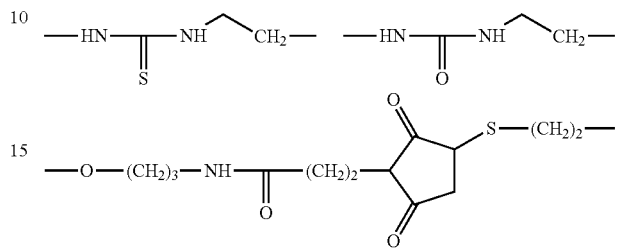

Advantageously, R' represents a group chosen from: a $C_1$-$C_3$ alkyl, for instance a methyl, an ethyl, an n-propyl or an isopropyl, and preferably a methyl or an ethyl.

Advantageously, $R^1$ represents a group chosen from: a $C_1$-$C_3$ alkyl, for instance a methyl, an ethyl, an n-propyl or an isopropyl, and even more advantageously a methyl.

Preferably, $Z^+$ represents a cation which may be chosen from: $K^+$, $Na^+$ and $NH_4^+$.

Preferably, $A^-$ represents an anion which may be chosen from: $Cl^-$, $Br^-$, $I^-$, acetate, propionate, butyrate, ascorbate, benzoate, cinnamate, citrate, fumarate, gycolate, malonate, tartrate, malate, maleate, mandelate and tosylate, and even more preferably $Cl^-$, $Br^-$, $I^-$, acetate and tosylate.

The porphyrins (I) which are preferred belong to the following list:

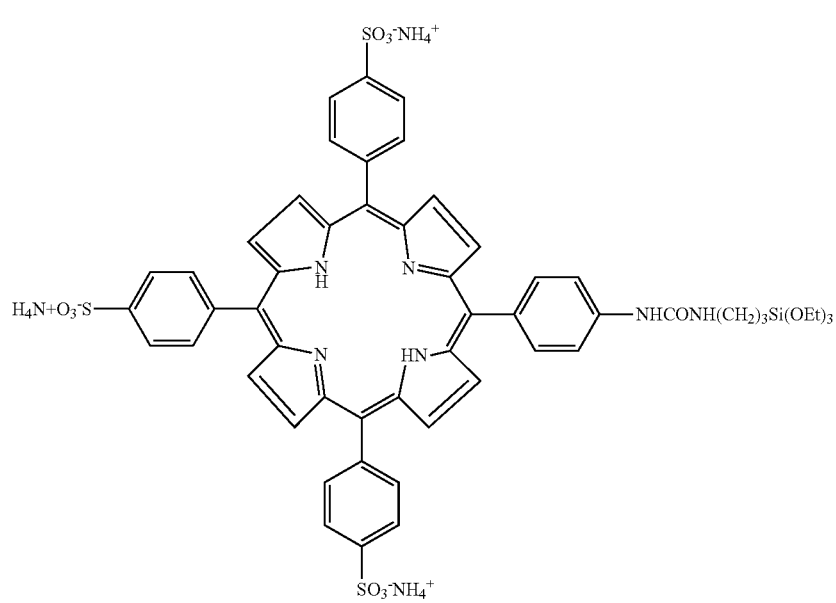

(IA)

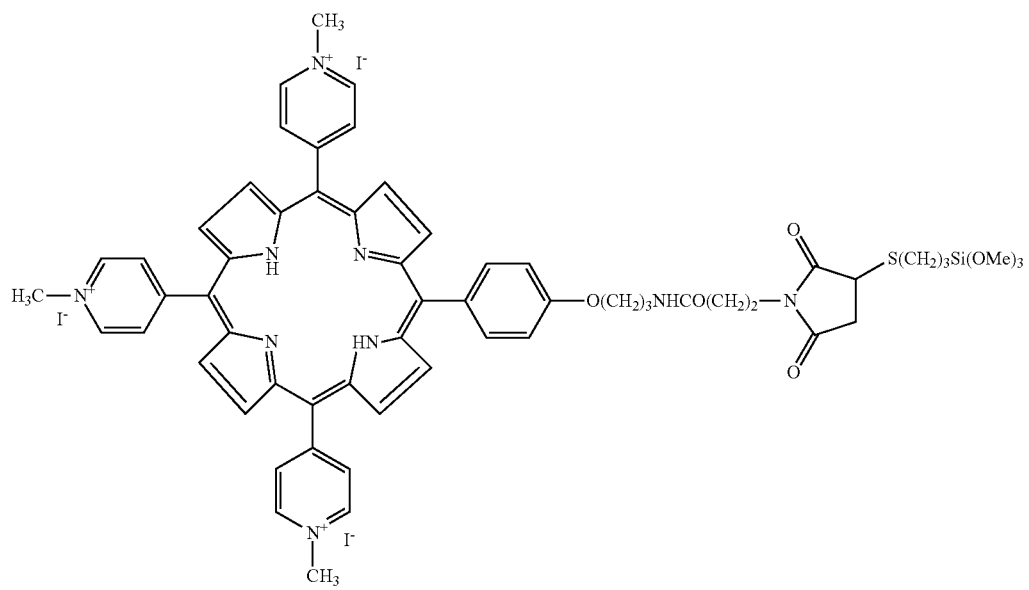

(IB)

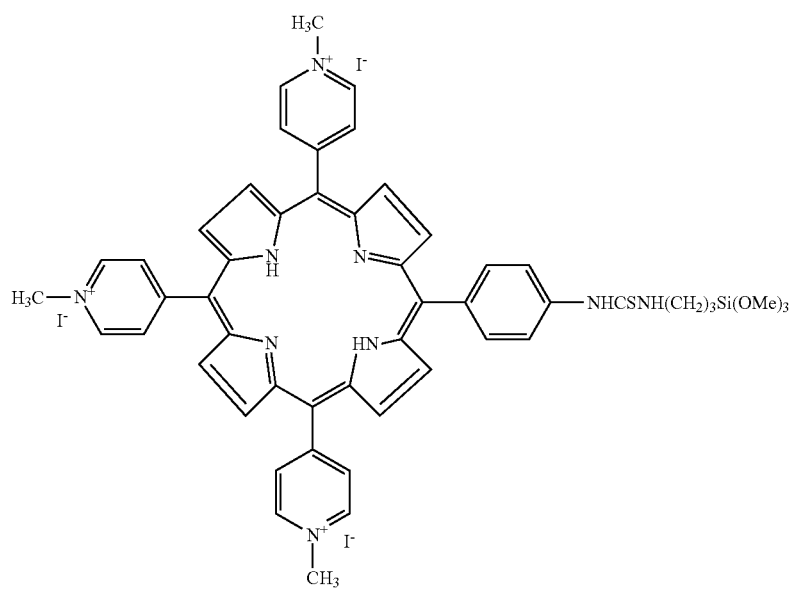

(IC)

The molecules corresponding to formula (I) are water-soluble photosensitizers which have a good ability to convert the molecular oxygen which surrounds them into reactive oxygen species. Owing to their water-solubility, they can be easily formulated in siliceous nanoparticles to which they are covalently bonded. In addition, the synthesis of these nanoparticles can be carried out in an essentially aqueous medium.

When R is chosen from:

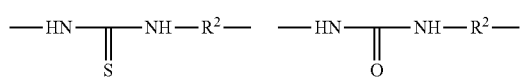

and $R^2$ represents a group chosen from a $C_1$-$C_{15}$ alkyl chain, optionally interrupted with one or more groups chosen from: an ether (—O—), an amine (—NH—), a thioether (—S—), a ketone (—CO—), an ester (—CO—O—), an amide (—CO—NH—), a urea (—NH—CO—NH—), a thiourea (—NH—CS—NH—), an oxycarbonyl (—O—CO—O—) and a carbamate (—NH—CO—O—), then the molecules of formula (I) can be prepared by means of a process as described in scheme 1 below, in which a porphyrin bearing an amine function (II) is reacted with an isocyanatotrialkoxysilane (or isothiocyanatoalkoxysilane when R represents NH—CS—NHR²) compound:

Scheme 1

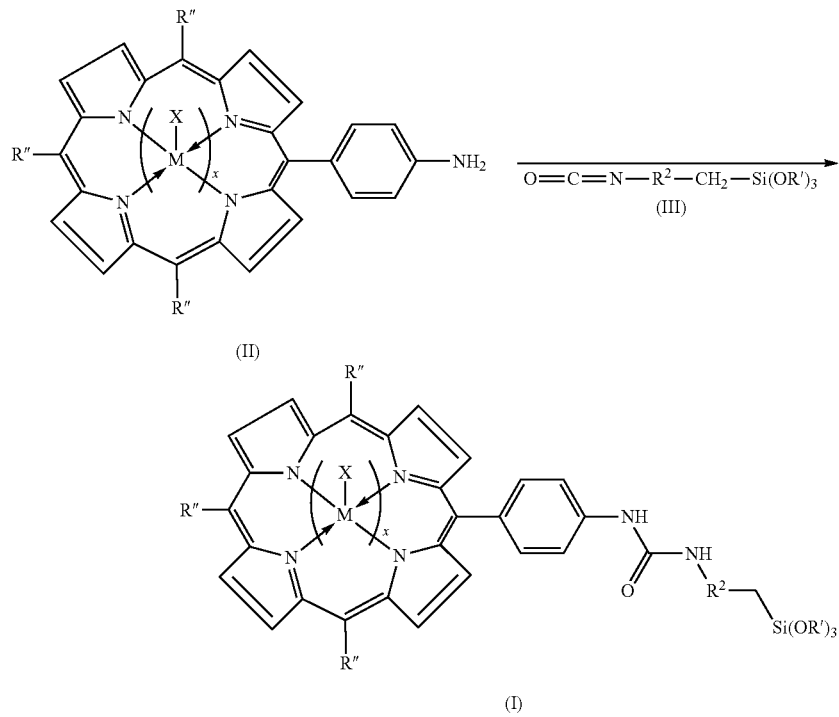

It is also possible to use a process according to scheme 2, in which a porphyrin bearing an isocyanate function (IV) (or isothiocyanate function when R represents NH—CS—NR$^2$) is reacted with an aminoalkyltrialkoxysilane compound (V):

When R represents a —CO—NH—R$^2$— group and R$^2$ represents a group chosen from a $C_1$-$C_{15}$ alkyl chain, optionally interrupted with one or more groups chosen from: an ether (—O—), an amine (—NH—), a thioether (—S—), a

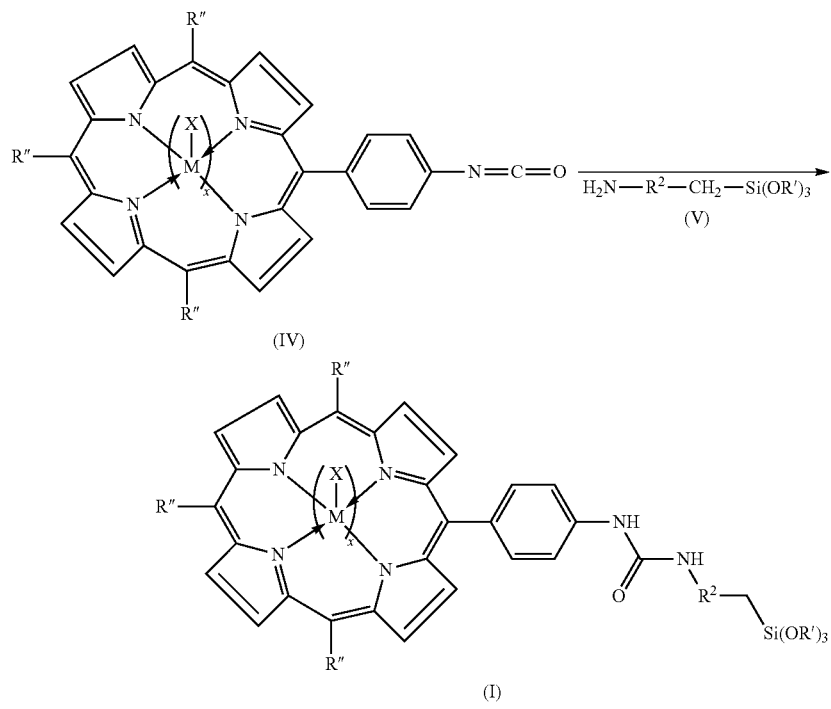

ketone (—CO—), an ester (—CO—O—), an amide (—CO—NH—), a urea (—NH—CO—NH—), a thiourea (—NH—CS—NH—), an oxy-carbonyl (—O—CO—O—) and a carbamate (—NH—CO—O—), it is then possible to carry out a coupling starting from a porphyrin bearing a carboxylic acid group according to scheme 3 below:

Scheme 3

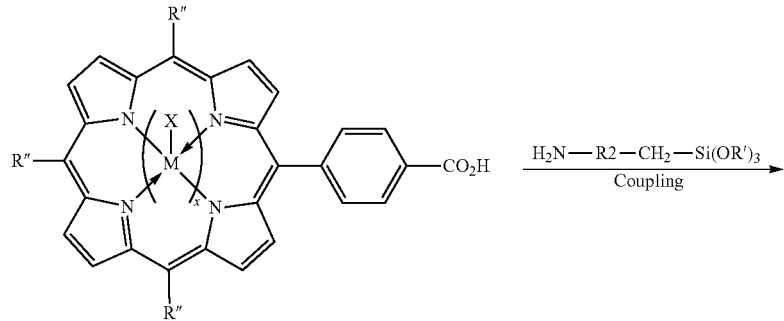

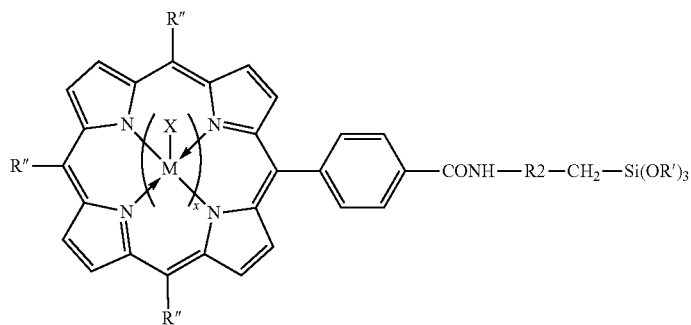

When R represents an —NH—R² — or —O—R² — group and R² represents a group chosen from a $C_1$-$C_{15}$ alkyl chain, optionally interrupted with one or more groups chosen from: an ether (—O—), an amine (—NH—), a thioether (—S—), a ketone (—CO—), an ester (—CO—O—), an amide (—CO—NH—), a urea (—NH—CO—NH—), a thiourea (—NH—CS—NH—), an oxycarbonyl (—O—CO—O—) and a carbamate (—NH—CO—O—), it is possible to carry out an SN2-type coupling, as illustrated respectively in scheme 4 and scheme 5.

Scheme 4

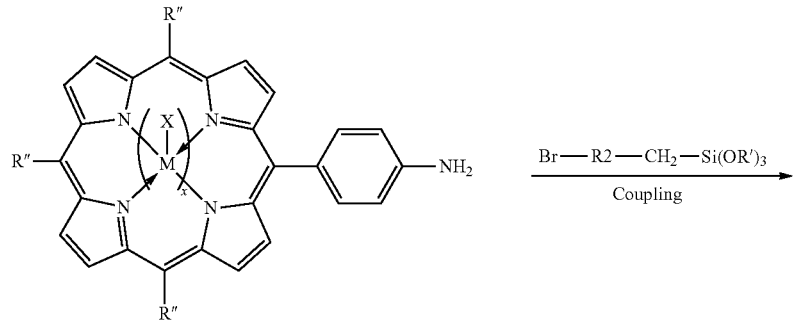

-continued

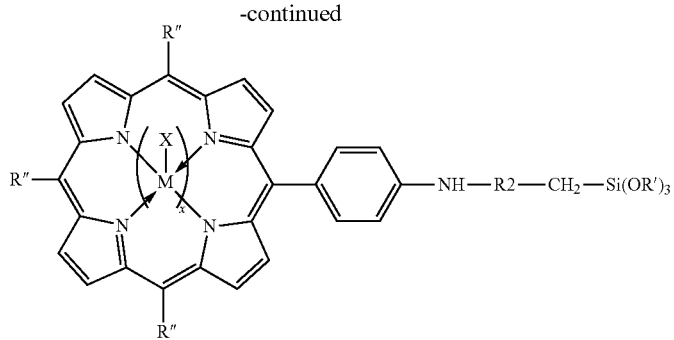

15

Scheme 5

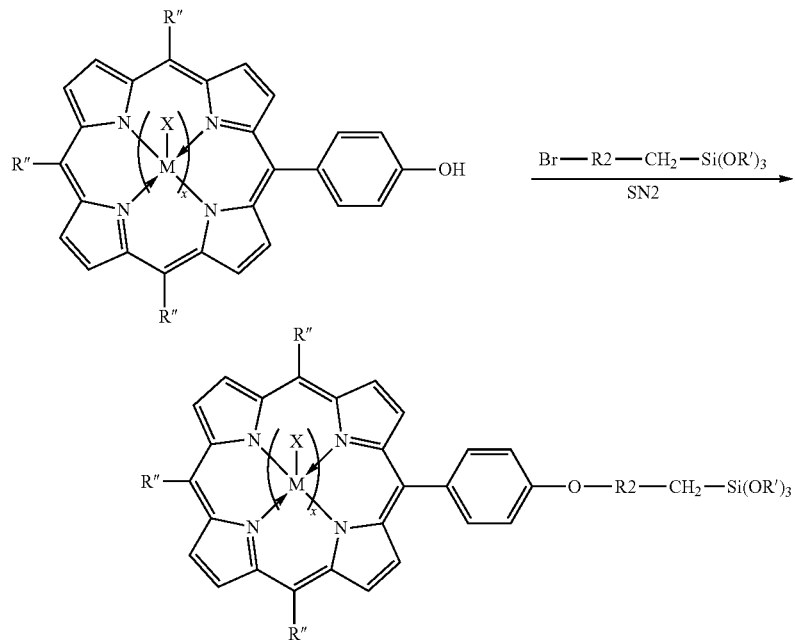

When R represents an —O—CO—NH—$R^2$— group and $R^2$ represents a group chosen from a $C_1$-$C_{15}$ alkyl chain, optionally interrupted with one or more groups chosen from: an ether (—O—), an amine (—NH—), a thioether (—S—), a ketone (—CO—), an ester (—CO—O—), an amide (—CO—NH—), a urea (—NH—CO—NH—), a thiourea (—NH—CS—NH—), an oxycarbonyl (—O—CO—O—) and a carbamate (—NH—CO—O—), it is possible to form a carbamate linker according to the method illustrated in scheme 6:

Scheme 6

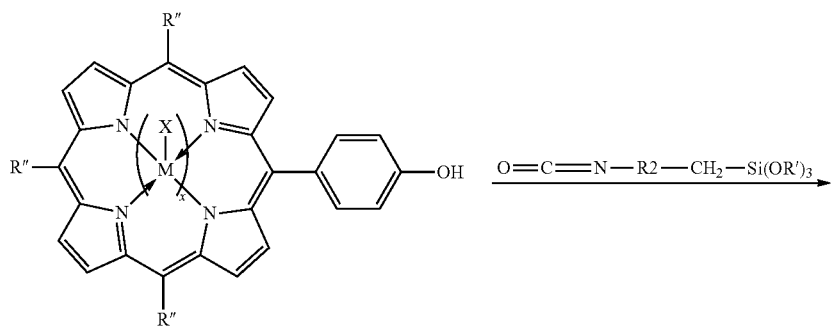

-continued

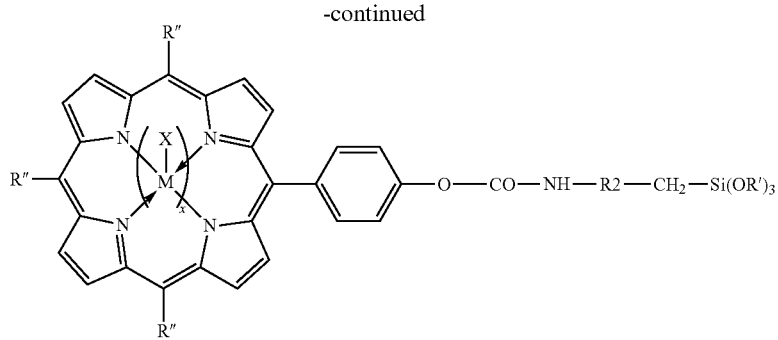

For the preparation of the porphyrins of formula (I), the following starting molecules may be used:

Cationic porphyrins bearing a phenyl-$CO_2H$ group are described in: H. Yamaguchi et al, Chem. Eur. J., 2004, 10, 6179. Anionic porphyrins bearing a —$CO_2H$ group are described in: U.S. Pat. No. 4,783,529. Anionic porphyrins bearing a hydroxyphenyl group are described in: EP 891977.

The synthesis of porphyrins bearing pyridine groups is described in particular in EP-345171. Such molecules can be used for preparing molecules of formula (I) as illustrated in scheme 7 below:

Scheme 7

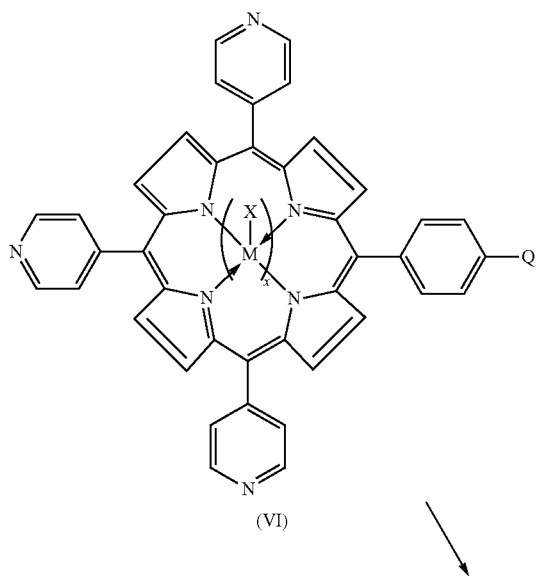

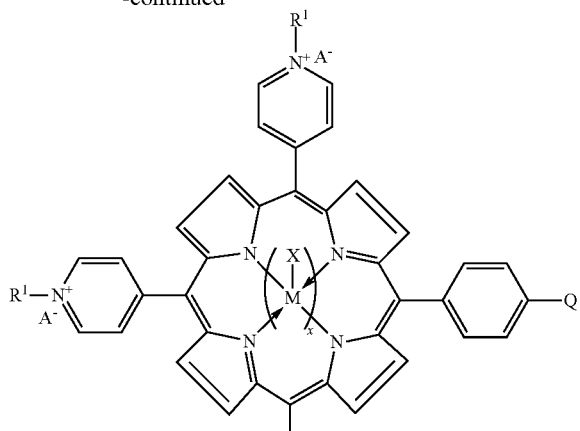

(VII)

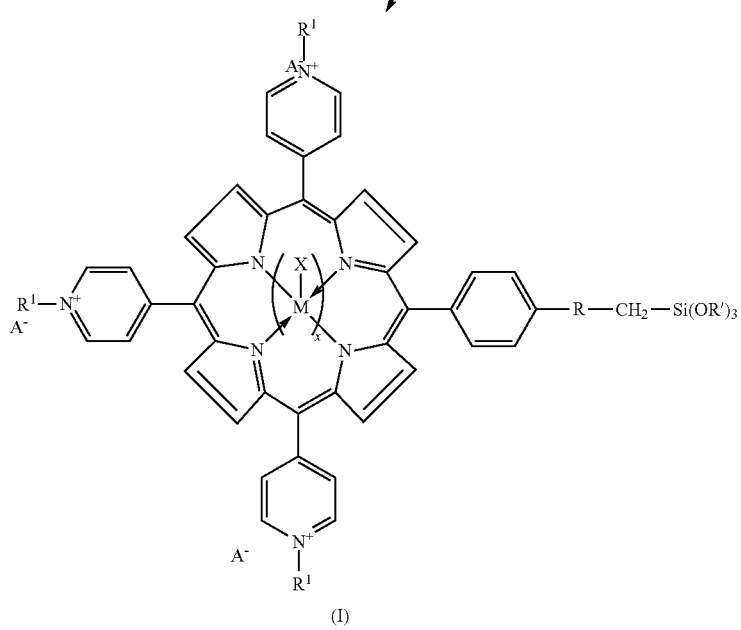

(I)

The starting product used is a porphyrin compound (VI) bearing three pyridine groups and an appropriate function Q, which is a precursor of a —R—CH$_2$— linker. The pyridine groups are then quaternized, to give (VII), and the Q group is converted and grafted with a trialkoxysilane group, to give (I).

A subject of the invention is also the compositions of nanoparticles comprising at least one photosensitizer corresponding to formula (I) above. These nanoparticles advantageously have an organized porosity.

The term nanoparticle having an organized porosity, or having a structured porosity, is intended to mean nanoparticles of which the pores are geometrically distributed according to a regular scheme in the three spatial dimensions. As an example of an organized porosity, mention may be made of a honeycomb structure.

The structured nature of the porosity can be observed in different ways:

The nanoparticles having an organized porosity have an X-ray diffraction spectrum.

The nitrogen adsorption/desorption method (BET) also makes it possible to characterize a structured porosity.

The fact of having a structure with an organized porosity facilitates the energy transfer from the photosensitizers to the oxygen and the release of reactive oxygen species, including singlet oxygen, in the cells. In addition, the porphyrins (I) are fluorescent if the metal cations M are diamagnetic or if x=0, and thus the nanoparticles of the invention make it possible to fluorescently label the zones where cancer tissues are located. In addition, some molecules of formula (I) include a paramagnetic metal cation (M in the porphyrin) which makes it possible to follow the distribution of the nanoparticles in the organism by NMR and MRI. The fact that these labeling molecules are in an organized structure, with a controlled porosity, facilitates the image analysis.

Advantageously, the nanoparticles of the invention are silica-based. The production of these nanoparticles comprises a step of polymerization of a siliceous precursor under conditions which allow the covalent grafting of the photosensitizer (I) and the formation of a network with an organized porosity.

According to a first variant, it is chosen to produce nanoparticles of mesoporous silica, formed by polymerization of a siliceous precursor in the presence of surfactants. The nanoparticles of mesoporous silica have the advantage of having a high specific surface area, a volume and pores of controlled size. The nanoparticles of the invention are advantageously monodisperse. The nanoparticles of mesoporous silica with a controlled porosity, of the invention, have a particle size ranging from 80 to 400 nm in diameter, a specific surface area ranging from 800 to 1000 $m^2/g$ and pores of size ranging from 2 to 6 nm. These nanoparticles are advantageously of MCM41 type.

Silica-based mesoporous nanoparticles and the process for the synthesis thereof have been described in particular in C. E. Fowler et al., Adv. Mater. 2001, 13, No. 9, 649-652. These are the same procedures which are used in the present invention.

The process for producing the nanoparticles of the invention is characterized in that tetraethoxysilane is polymerized in a basic aqueous solution in the presence of a surfactant, such as cetyltrimethylammonium bromide, and in the presence of the molecule of formula (I).

According to a second variant, it is chosen to produce microporous silica nanoparticles. The microporous nanoparticles of the invention are of silicalite type and are synthesized in a basic medium in the presence of the molecule of formula (I), of tetraethoxysilane and of a structuring agent of quaternary ammonium type (for instance tetrapropylammonium hydroxide). The nanoparticles of the invention are advantageously monodisperse. The nanoparticles of the invention are then microporous with a diameter of between 30 and 80 nm, a specific surface area ranging from 100 to 450 $m^2/g$ and pore diameters ranging from 2 to 20 Å.

Silica-based microporous nanoparticles and the process for the synthesis thereof have been described in particular in T. Doussineau et al., Eur. J. Inorg. Chem. 2006, 2766-2772. These are the same procedures that are used in the present invention.

The processes for producing these nanoparticles result in the formation of a covalent bond between the molecules of formula (I) and the nanoparticles, thereby avoiding release of the molecules of formula (I) in the organism and promoting the conveyance thereof specifically to their biological target.

Figure 4:
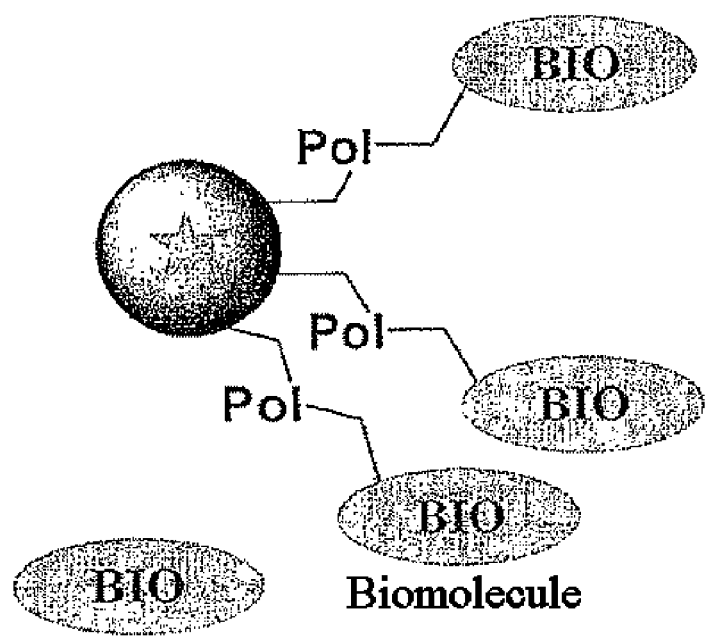
Figure 4:

Preferably, the nanoparticles of the invention are grafted, on their surface, with targeting molecules specific for neoplastic tissues, i.e. biomolecules of which the receptors are overexpressed by cancer cells, or at the surface of cancer cells. These targeting molecules facilitate the transfer of the nanoparticles to their biological target. Generally, these targeting molecules can be chosen from: folic acid, peptides and carbohydrates. They can be grafted onto the nanoparticles of the invention by means of a polymeric linker, as illustrated in FIG. 4.

Figure 5:
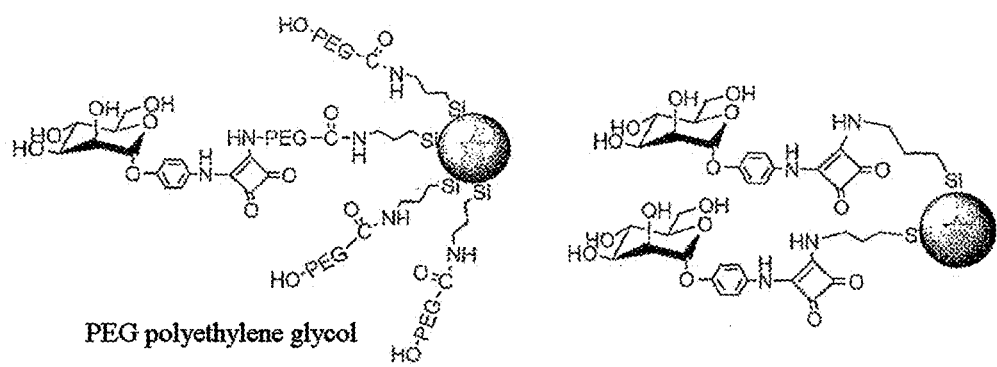

Among the targeting molecules that can be grafted onto the nanoparticles of the invention, mention may be made of:

derivatives of sugar, such as mannose, which can be grafted onto siliceous nanoparticles by means of a polyethyleneimine linker or a polyethylene glycol PEG linker. The grafting of mannose onto mesoporous silica nanoparticles is described in particular in I. Young Park et al., International Journal of Pharmaceutics, 359, 2008, 280-287, and the same procedures can be used. Another approach consists in using phenylsquarate-α-mannose as illustrated in FIG. 5;

peptides such as peptides with a hormonal target (LH—RH);

glycodendrimers bearing several monosaccharide or disaccharide derivatives, such as mannose, mannose-6-phosphate, glucose, galactose, etc.

Methods for grafting silica-based microporous nanoparticles with biomolecules have been described in particular in T. Doussineau et al., Eur. J. Inorg. Chem. 2006, 2766-2722 and the same procedures can be used.

A subject of the invention is also a process for producing a medicament intended for the treatment and/or prevention and/or detection of tumors, comprising the nanoparticle production step described above.

The production of singlet oxygen and therefore the destruction of the cancer cells is induced by photon excitation: after irradiation of the nanoparticles with a light source, the singlet oxygen generated makes it possible to destroy the tumor cells. The irradiation is carried out at a wavelength of between 630 nm and 680 nm at a power ranging from 2 to 10 $mW/cm^2$. The results obtained show that the nanoparticles synthesized are effective for generating singlet oxygen in solution with a quantum yield of between 30% and 90%. These nanoparticles should allow vectorization of active ingredients and endocytosis thereof in tumor cells after surface-functionalization with biomolecules.

Among the various cancers that it is possible to envision treating with the nanoparticles of the invention, mention may be made of: retinoblastoma (Y-79 cell lines), colon cancer (HT29 cell lines), epidermal cancer (A 431), lung cancer (A 549), breast cancer (MDA-MB-231, MCF-7), cervical cancer (HeLa), ovarian cancer (PEO14) and also all the solid tumors, including, but not limited to, head and neck cancers, gastrointestinal and sex-organ cancers, and any benign or cancerous tumor which can be illuminated.

After endocytosis, the cell lines are irradiated in one of the absorption bands of the photosensitizer, and the effectiveness of the nanoparticles is evaluated by means of an MTT assay.

The compositions of nanoparticles of the invention can be administered locally or systemically. Local administration can be carried out in particular by injection of the nanoparticle composition in the vicinity of the tumor zone. In the case of superficial tumors, the nanoparticle compositions can be administered topically, in a suitable galenical form (solution, suspension, paste, patch). General administration can be carried out intravenously, intramuscularly, subcutaneously, intraperitoneally or rectally. Such formulations and their mode of use are well known to those skilled in the art.

The dosage of the composition in terms of active agent of formula (I) is adjusted according to the weight and age of the patient, to the nature, location and stage of development of the tumor, to the route of administration chosen and to the dose of irradiation used.

The composition may comprise any other active ingredient known for the treatment of tumors and/or of symptoms thereof. It comprises the conventional components of galenics suitable for the mode of administration chosen.

A subject of the invention is also the nanoparticles described above, for their use as a medicament, in particular for the prevention and/or treatment of tumors and cancers.

EXPERIMENTAL SECTION

Figures:

FIG. 1: X-ray diffractogram of the silicalite nanoparticles encapsulating an anionic porphyrin.

Figure 2:
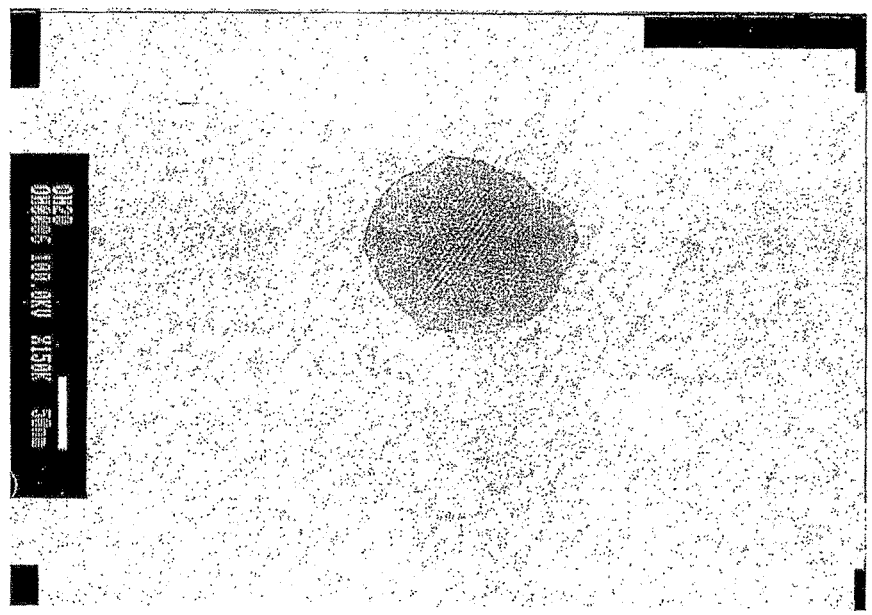

FIG. 2: TEM photograph of a mesoporous nanoparticle with an organized porosity.

Figure 3:
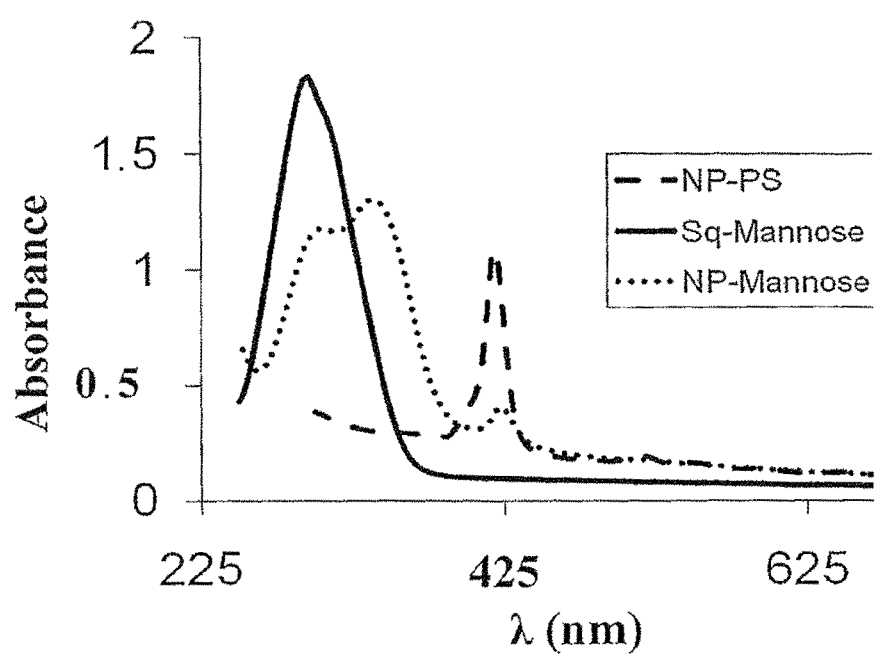

FIG. 3: UV spectrum of the nanoparticles DG015 (NP-PS), DB016 (NP-mannose) and of arylsquarate-α-mannose (Sq-mannose).

FIG. 4: nanoparticles of the invention grafted with targeting molecules.

FIG. 5: example of mannose-functionalized nanoparticles.

FIGS. 6 to 14: biological results regarding the cytotoxic efficacy of various nanoparticles encapsulating photosensitizers on breast cancer (MDA-MB-231), ovarian cancer (POE14), prostate cancer (LNCaP) and retinoblastoma (Y-79) cell lines after single-photon excitation.

I—SYNTHESIS OF THE MOLECULES OF FORMULA (I)

A—Synthesis of the Water-Soluble Cationic Porphyrin 8

Synthesis Scheme

The compound 3 (1 equivalent) obtained by means of the method described by Diane L. Dick et al, J. Am. Chem. Soc. 1992, 114, 2664-2669, is condensed according to the standard Adler procedure, with the pyridine aldehyde (3 equivalents) and the pyrrole (4 equivalents) to give, after chromatography, the porphyrin 4 with a yield of 5.7%, as described by Martine Perrée-Fauvet et al. for the analogous meta compound, Tetrahedron. 1996, 52, 13569-13588. The derivative 5 is obtained quantitatively from the compound 4 by treatment with hydrazine in water at reflux. The reaction of the porphyrin 5 and the peptidic acid 6 in dichloromethane, in the presence of 1-hydroxybenzotriazole hydrate (HOBt), 1-(3-dimethyl-aminopropyl)-3-ethylcarbodiimide hydrochloride (EDC) and triethylamine as coupling agents, gives the compound 7 (yield: 40%) (Daniel H. Rich, et al., *J. Med. Chem.* 1975, 18, 1004-1010). The latter compound is treated with a large excess of methyl iodide to give, quantitatively, the water-soluble porphyrin 8.

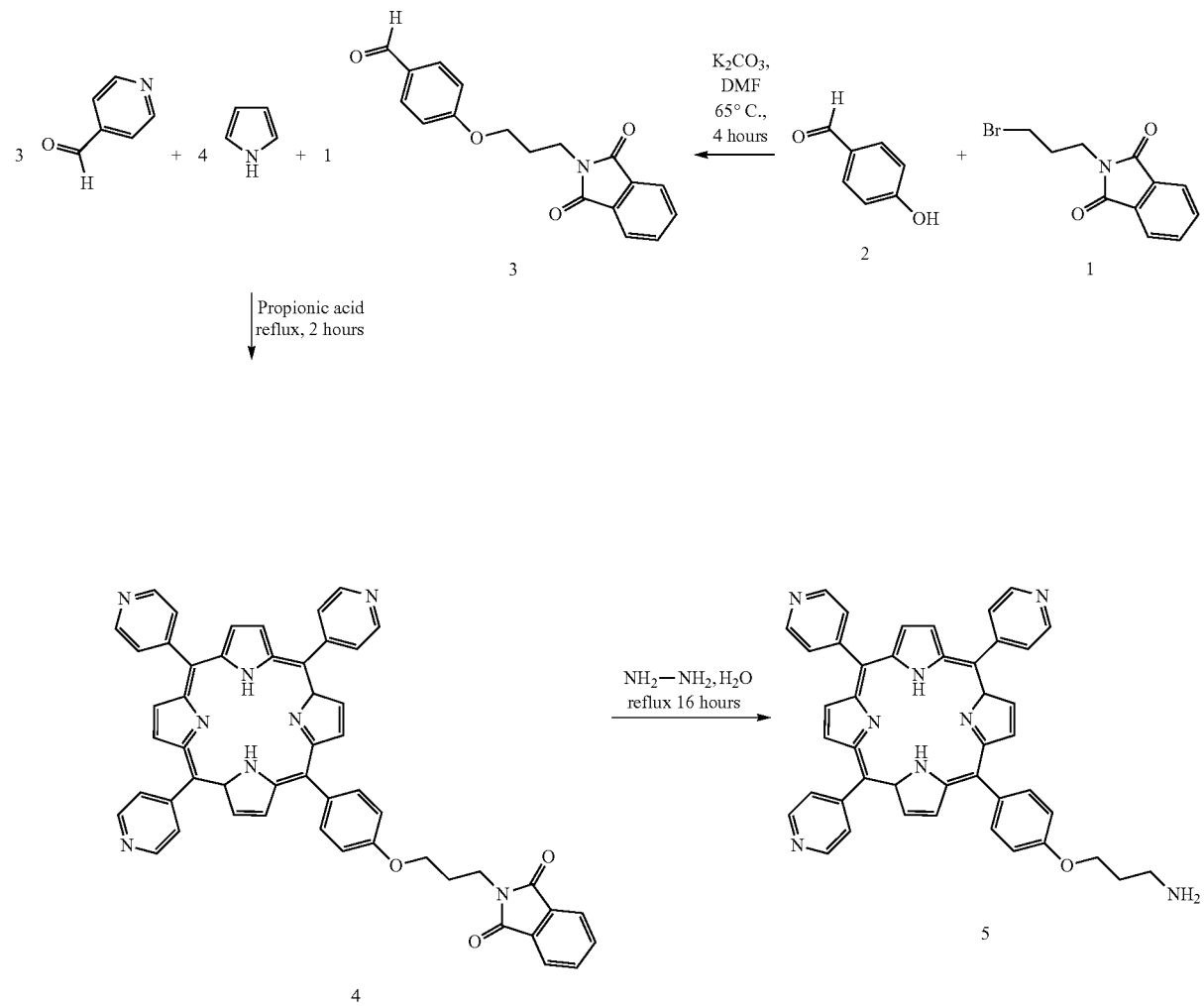

-continued
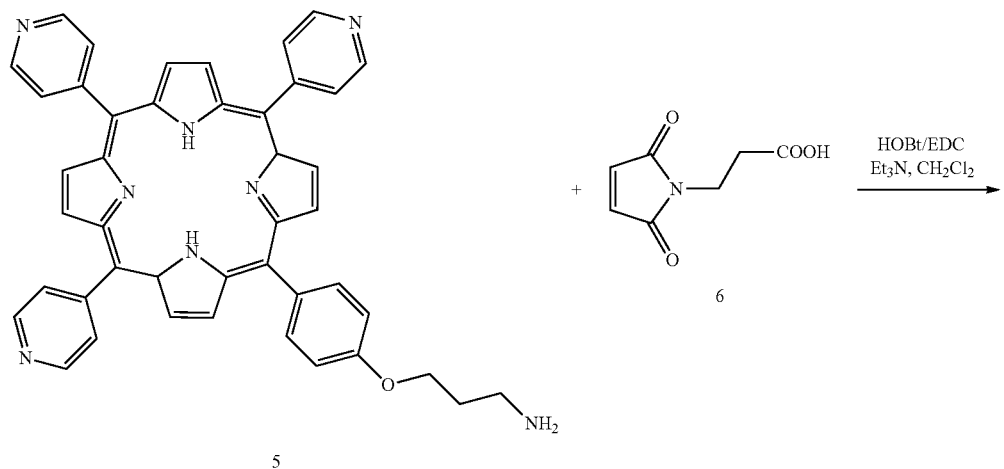
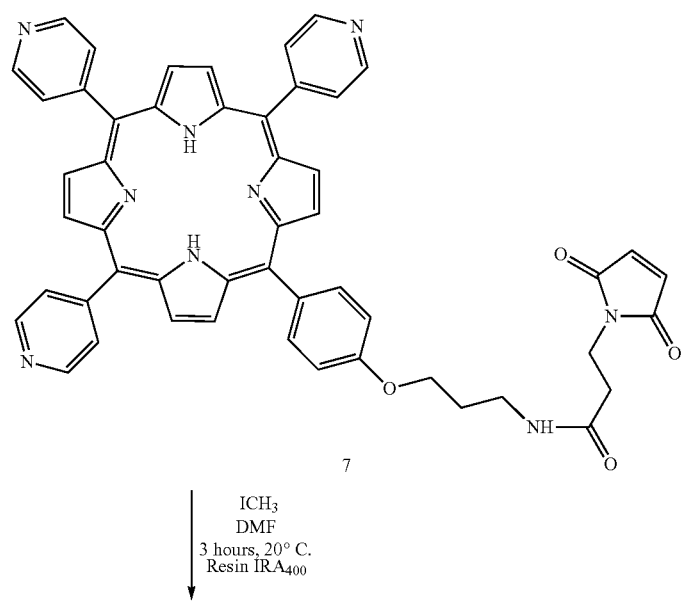

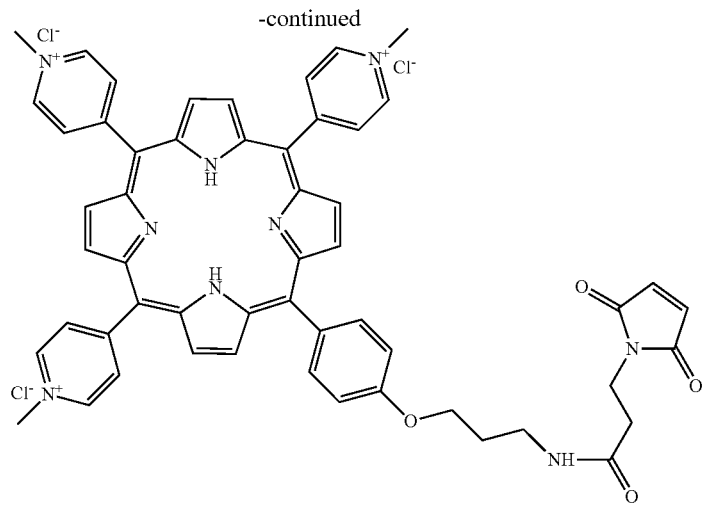

Procedures

5-[p-(3-Isoindoline-1',3'-dionepropoxy)phenyl]-10,15,20-tri-p-pyridylporphyrin 4

The porphyrin 4 is prepared from the aldehyde 3 (6.2 g, 20 mmol) and 4-pyridinecarboxaldehyde (6.4 g, 60 mmol) which are dissolved in boiling propionic acid (400 ml). The pyrrole (5.36 g, 80 mmol) is then added dropwise. Reflux is maintained for 2 h. The solution is evaporated under vacuum. A first purification by silica gel chromatography, elution being carried out with a $CH_2Cl_2$/EtOH mixture (100/5, v/v), is carried out in order to eliminate the maximum amount of impurities. A second, in which elution is carried out with $CH_2Cl_2$ and then an increasing amount of ethanol (0 to 10%), allows the separation of the six porphyrins. The 5,10,15-tripyridyl-20-phenylporphyrin 4 is eluted (third fraction) with a $CH_2Cl_2$/EtOH mixture (94/6, v/v) and is obtained after crystallization, with a dichloro-methane/methanol mixture, in the form of blue crystals (yield: 5.7%). UV-vis spectrum in $CH_2Cl_2$: $\lambda_{max}$, nm (OD): 418.5 (1), 514.5 (0.61), 549 (0.31), 589 (0.25), 646 (0.16). $^1$H NMR (300 MHz, $CDCl_3$) δ 9.05 (m, 6H, meta-pyridine), 8.95 (d, J=4.7 Hz, 2H, pyrrole), 8.85 (s, 4H, pyrrole), 8.81 (d, J=5 Hz, 2H, pyrrole), 8.16 (d, J=5.8 Hz, 6H, ortho-pyridine), 8.07 (d, J=8.4 Hz, 2H, meta-phenyl), 7.93 (dd, J=3.1, 5.4 Hz, 2H, phthalimide), 7.76 (dd, J=3.0, 5.4 Hz, 2H, phthalimide), 7.12 (d, J=8 Hz, 2H, ortho-phenyl, 4.35 (t, 8 Hz, 2H, O—$CH_2$), 4.09 (t, 8 Hz, 2H, N—$CH_2$), 2.40 (m, 2H, $CH_2$), −2.87 (s, 2H, NH).

5-[p-(3-Aminopropoxy)phenyl]-10,15,20-tri-p-pyridylporphyrin 5

A mixture of porphyrin 4 (0.930 g, 1.13 mmol) and of hydrazine monohydrate (0.71 ml, 23 mmol) is brought to reflux for 16 h, and then stirred, at ambient temperature, for 24 h. The phthalhydrazide is precipitated by adding HCl (10% solution) and filtered off. The solution is neutralized by adding NaOH (10% solution). The porphyrin is extracted from the aqueous phase with a $CH_2Cl_2$/EtOH mixture (95/5, v/v). After drying over sodium sulfate, filtration and evaporation to dryness, the porphyrin 5 (0.760 g) is obtained pure in the form of a blue powder (yield: 97%). UV-vis spectrum in $CH_2Cl_2$: $\lambda_{max}$, nm (ϵ L.mmol$^{-1}$.cm$^{-1}$): 418 (224.9), 515 (13.1), 550 (6.5), 590 (5.4), 647 (4.1). $^1$H NMR (300 MHz, $CDCl_3$) δ 9.05 (m, 6H, meta-pyridine), 8.95 (d, J=4.7 Hz, 2H, pyrrole), 8.85 (s, 4H, pyrrole), 8.81 (d, J=5 Hz, 2H, pyrrole), 8.16 (d, J=5.8 Hz, 6H, ortho-pyridine), 8.10 (d, J=8.4 Hz, 2H, meta-phenyl), 7.31 (d, J=8 Hz, 2H, ortho-phenyl), 4.38 (t, J=8 Hz, 2H, O—$CH_2$), 3.09 (t, J=8 Hz, 2H, N—$CH_2$), 2.14 (m, 2H, $CH_2$), −2.87 (s, 2H, NH).

5-{p-[3-(2',5═-Dioxo-2',5'-dihydro-1H-pyrrol-1'-yl-N-(3-phenoxypropyl)propanamide]phenyl}-10,15,20-tri-p-pyridylporphyrin 7

The compound 5 (160 mg, 0.23 mmol) is dissolved in $CH_2Cl_2$ (40 ml). HOBt (48 mg, 0.35 mmol), EDC (67 mg, 0.35 mmol), triethylamine (48 ml, 0.35 mmol) and 5-(2,5-dioxo-2,5-dihydropyrrol-1-yl)propionic acid (80 mg, 0.46 mmol) are added. The mixture is stirred under argon, for three hours, at ambient temperature. The end of the reaction is verified by analytical thin layer chromatography on silica gel, elution being carried out with a $CH_2Cl_2$/ethanol mixture (90/10, v/v). The solution is diluted with a mixture of $CH_2Cl_2$/ethanol (95/5, v/v) and washed with water (×3), dried over sodium sulfate, filtered, and then concentrated under vacuum. The product is purified by thin layer chromatography ($Al_2O_3$), elution being carried out with a mixture of $CH_2Cl_2$/methanol (9/1, v/v). The compound 7 is obtained in the form of a blue powder after crystallization from a CH$_2$Cl$_2$/ethanol/heptane mixture (110 mg, yield: 57%). UV-vis spectrum in CH$_2$Cl$_2$: $\lambda_{max}$, nm ($\epsilon$ L.mmol$^{-1}$.cm$^{-1}$): 418 (190.6), 516 (13.7), 550 (8.3), 591 (7.1), 652 (6.7). Electrospray mass spectrum: cal. for C$_{51}$H$_{39}$N$_9$O$_4$ 841.9 found 842.66 M+1. $^1$H NMR (300 MHz, CDCl$_3$) δ 9.04 (d, J=5.6 Hz, 6H, meta-pyridine), 8.92 (d, J=5 Hz, 2H, pyrrole), 8.83 (s, 4H, pyrrole), 8.80 (d, J=4.7 Hz, 2H, pyrrole), 8.13 (d, J=5.7 Hz, 6H, ortho-pyridine), 8.10 (d, J=8.5 Hz, 2H, meta-phenyl), 7.30 (d, J=8.6 Hz, 2H, ortho-phenyl), 4.32 (t, 8 Hz, 2H, O—CH$_2$), 3.92 (t, J=7.4 Hz, 2H, CH$_2$—N), 3.63 (t, J=7.8 Hz, 2H, CH$_2$—NH—CO), 2.62 (t, J=7 Hz, 2H, CH$_2$—CO—NH), 2.19 (t, 2H, CH$_2$), -2.87 (s, 2H, NH). $^{13}$C NMR (300 MHz, CDCl$_3$) δ 170.6 (CON), 169.7 (CO—NH), 158.8 (para-phenyl), 150 (pyridine), 148.4 (meta-pyridine), 135.7 (ortho-phenyl), 134.3 (ethylene), 134 (phenyl), 131 (pyrrole), 129.4 (ortho-pyridine), 121.6 (meso-C), 117.4 (meso-C), 116.7 (meso-C), 112.8 (meta-phenyl), 66.6 (C—O—), 37.5 (C—NHCO), 34.9 (C—N), 34.3 (C—CONH), 29.2 (C—C—O).

5-{p-[3-(2',5'-Dioxo-2',5'-dihydro-1H-pyrrol-1'-yl)-N-(3-phenoxypropyl)propanamide]phenyl]-10,15,20-tri-p-pyridiniumporphyrin trichloride 8

The porphyrin 7 (68 mg, 0.08 mmol) and methyl iodide (1 ml) are dissolved in dimethylformamide (20 ml) and stirred at ambient temperature for three hours. The solution is concentrated under vacuum and then diluted with methanol (10 ml). IRA 400 resin (0.9 g) is added to the solution and then the suspension is gently stirred for 1 hour 30. The solution is filtered and then evaporated. The pure compound is obtained in the form of a blue powder after crystallization from a methanol/diethyl ether mixture (80 mg, yield: 100%). UV-vis spectrum in MeOH: $\lambda_{max}$, nm (µL.mmol$^{-1}$.cm$^{-1}$): 427 (98.3), 518 (12), 557 (6.1), 593 (4.1), 652 (2.5). MALDI-TOF mass spectrum: calc for C$_{54}$H$_{48}$N$_9$O$_4$Cl$_3$ 993.38, found 886.44, M−3Cl$^-$, 887.44, M+H−3Cl$^-$.

B—Synthesis of the Water-Soluble Anionic Porphyrin 9

This compound is prepared by means of the method described by Kruper et al., J. Org. Chem. 1989, 54, 2753-2756, from 5,10,15,20-tetraphenylporphyrin with an overall yield of 43%.

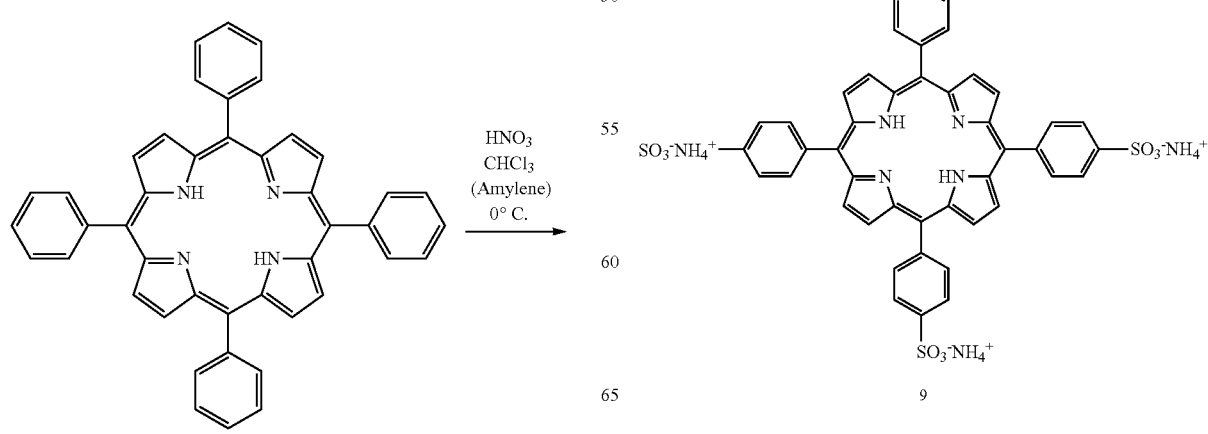

II—SYNTHESIS OF THE NANOPARTICLES

A—Synthesis of Mesoporous Nanoparticles Encapsulating an Anionic Porphyrin

DB 003, DB 005 Nanoparticles

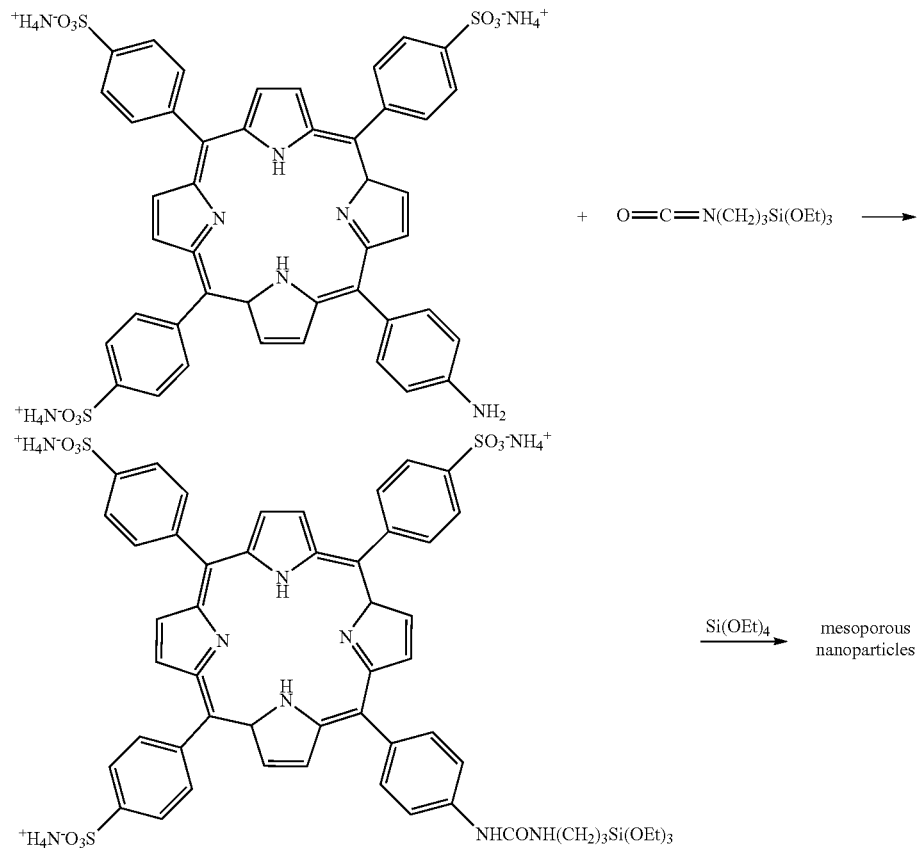

DB 003: 5 mg of the porphyrin 9 ($5.44 \times 10^{-3}$ mmol) are dissolved in 1 ml of EtOH by subjecting to ultrasound for 15 min. 5 equivalents ($2.72 \times 10^{-2}$ mmol) of isocyanatopropyltriethoxysilane are added, as are 4 equivalents ($2.17 \times 10^{-2}$ mmol) of diisopropylethylamine. The solution is maintained at ambient temperature for 12 hours.

686 mg ($1.8 \times 10^{-3}$ mol) of cetyltrimethylammonium bromide (CTAB) are dissolved in 40 ml of 0.2M sodium hydroxide at 25° C. The solution previously prepared is added, and then tetraethoxysilane (3.5 ml, $1.57 \times 10^{-2}$ mmol) is added dropwise. After 40 seconds, 260 ml of deionized water are added. The solution is kept stirring for 6 minutes and then rapidly neutralized to pH 7 by adding 0.2 M HCl (approximately 50 ml). The nanoparticles are recovered by centrifugation (20 minutes, 20 000 rpm), resuspended in EtOH with ultrasound, and centrifuged. The surfactant is extracted by treatment with 30 ml of EtOH/12N HCl (4/1) solution for 2 h at 60° C. After centrifugation, the operation is repeated twice, and then the nanoparticles are resuspended in water and centrifuged until a neutral pH is obtained (5 times).

Alternatively, the surfactant can be eliminated by treatment with ammonium nitrate (Chem Mater, 2004, 10, 1961): 300 mg of $NH_4NO_3$ are dissolved in 150 ml of 95% EtOH. 500 mg of nanoparticles are suspended in this solution and treated with ultrasound for 15 minutes, and then the solution is placed at 60° C. for 15 min. The suspension is recovered by centrifugation, redispersed with ultrasound in EtOH, and centrifuged. The surfactant extraction protocol is repeated once.

Transmission electron microscopy (TEM) shows the presence of a hexagonal network of mesopores with a nanoparticle diameter of about 100 nm.

Quasi-elastic light scattering (DLS) confirms the hydrodynamic diameter of 150 nm.

BET indicates a specific surface area of 862 $m^2$/g and a pore diameter of 2 nm.

UV-visible absorption spectroscopy analysis, termed UV analysis, (EtOH) confirms the presence of the covalently encapsulated porphyrin; a load of 3.3 µmol of porphyrin per g of nanoparticles is obtained.

The ability of the nanoparticles to generate singlet oxygen is evaluated by phosphorescence thereof after irradiation in one of the absorption bands of the photosensitizer, and in particular at 421 nm, of 3 mg of nanoparticles in 5 ml of absolute EtOH. The quantum yield for singlet oxygen formation is 92%.

The same procedure is used to synthesize the DB 005 nanoparticles, but 10 mg ($10.88 \times 10^{-3}$ mmol) of the porphyrin 9, 13.4 µl of isocyanatopropyltriethoxysilane and 7.4 µl of diisopropylethylamine are used.

Transmission electron microscopy (TEM) shows the presence of a hexagonal network of mesopores with a nanoparticle diameter of about 100 nm.

Quasi-elastic light scattering (DLS) confirms the hydrodynamic diameter of 200 nm.

BET indicates a specific surface area of 891 $m^2$/g and a pore diameter of 2 nm.

UV-visible absorption spectroscopy analysis, termed UV analysis, (EtOH) confirms the presence of the covalently encapsulated porphyrin; a load of 6.94 μmol of porphyrin per g of nanoparticles is obtained.

The ability of the nanoparticles to generate singlet oxygen is evaluated by phosphorescence thereof after irradiation in one of the absorption bands of the photosensitizer, and in particular at 421 nm, of 3 mg of nanoparticles in 5 ml of absolute EtOH. The quantum yield for singlet oxygen formation is 32%.

B—Grafting of Aminopropyltriethoxysilane (APTS) at the Surface of the Nanoparticles DB 015, DB 019 Nanoparticles

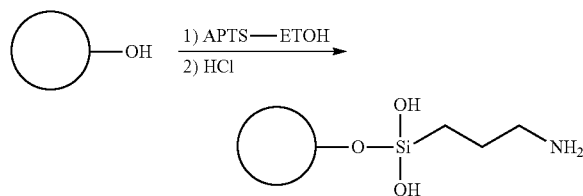

DB 015: 250 mg of the DB 003 nanoparticles are suspended in 6 ml of deionized $H_2O$ with ultrasound for 30 min. A solution of 2.5 ml of EtOH and 391 μl of APTS is then added dropwise. 0.2M HCl is added to pH=6. The reaction is stirred for 20 h, and centrifuged for 15 min at 20 000 rpm. The nanoparticles are washed with EtOH (ultrasound+centrifugation) and then washed with EtOH in a Soxhlet apparatus for 20 h. The mass m of particles obtained=206 mg.

The amine functions are characterized by a qualitative ninhydrin test.

UV analysis (EtOH) indicates that the porphyrin is still present and has not been modified during the reaction.

BET indicates that the specific surface area has decreased to 481 $m^2/g$, owing to the presence of the aminopropyl groups at the surface of the nanoparticles, but also in the pores.

The APTS is quantitatively determined by microanalysis and $^{29}Si$ NMR of the solid. An amino load of 2.2 mmol/g is obtained.

The same procedure is used to synthesize the DB 019 nanoparticles from the DB 005 nanoparticles.

BET indicates that the specific surface area has decreased to 545 $m^2/g$, owing to the presence of the aminopropyl groups at the surface of the nanoparticles, but also in the pores.

C—Synthesis of the Silicalite Nanoparticles Encapsulating an Anionic Porphyrin

DB 008 Nanoparticles

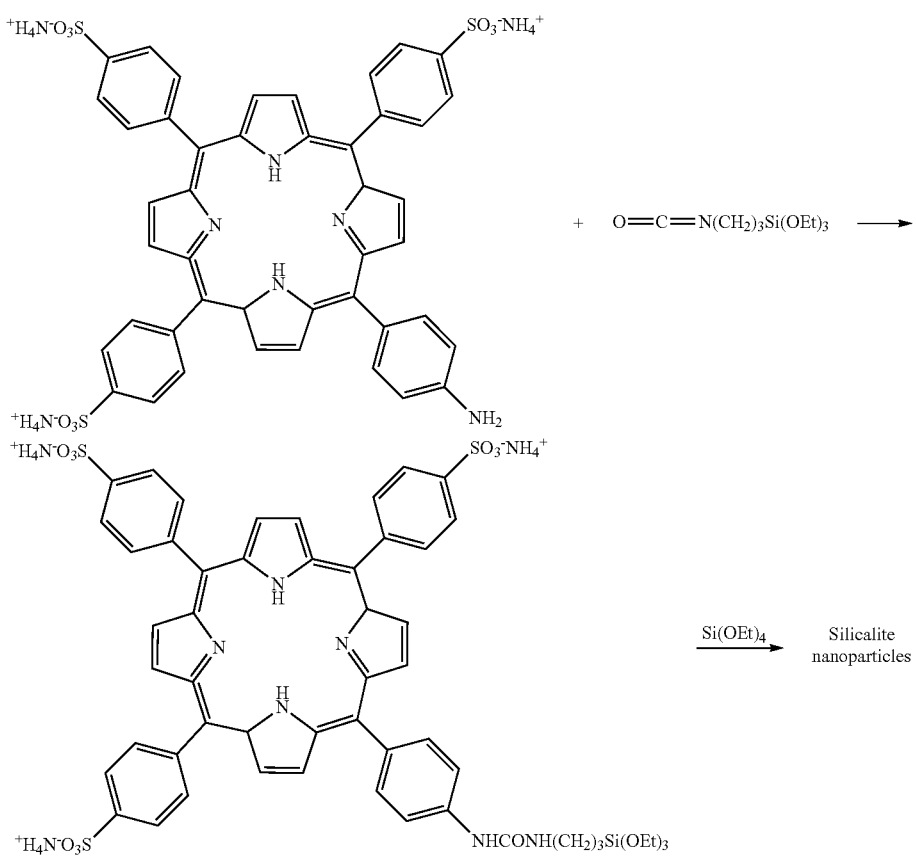

4 mg of the porphyrin 9 (4.35×10$^{-3}$ mmol) are dissolved in 1 ml of EtOH by subjecting to ultrasound for 15 min. equivalents (4.5 µl) of isocyanatopropyltriethoxysilane are added, as are 4 equivalents (3.04 µl) of diisopropylethylamine. The solution is maintained at ambient temperature for 12 h, and then 14 ml of 1M tetrapropylammonium hydroxide in water, 8.4 ml of TEOS and 2 ml of water are added and the reaction is maintained at ambient temperature for 24 h. The solution is then placed in an oven at 80° C. without stirring for 48 h. After cooling, the solution is centrifuged 3 times for 20 minutes at 20 000 rpm. The nanoparticles are then redispersed in water and centrifuged. The extraction of the structuring agent is carried out with an EtOH/12N HCl (4/1) solution for 2 h at 60° C. Two cycles are carried out. The nanoparticles are then washed with H$_2$O 6 times (6 cycles of dispersion in water with ultrasound and centrifugation) until a pH of 3.5 is obtained. The nanoparticles are then washed twice with EtOH.

Powder X-ray analysis of the nanoparticles is carried out, and the analysis shows the presence of a structured network characteristic of zeolites (FIG. 1).

DLS gives a hydrodynamic radius of 68 nm.
BET gives a specific surface area of 300 m$^2$/g.

The ability of the nanoparticles to generate singlet oxygen is evaluated by phosphorescence thereof after irradiation in one of the absorption bands of the photosensitizer, and in particular at 421 nm, of 3 mg of nanoparticles in 5 ml of absolute EtOH. The quantum yield for singlet oxygen formation is 31%.

D—Synthesis of the Silicalite Nanoparticles Encapsulating a Cationic Porphyrin

DB 011 Nanoparticles

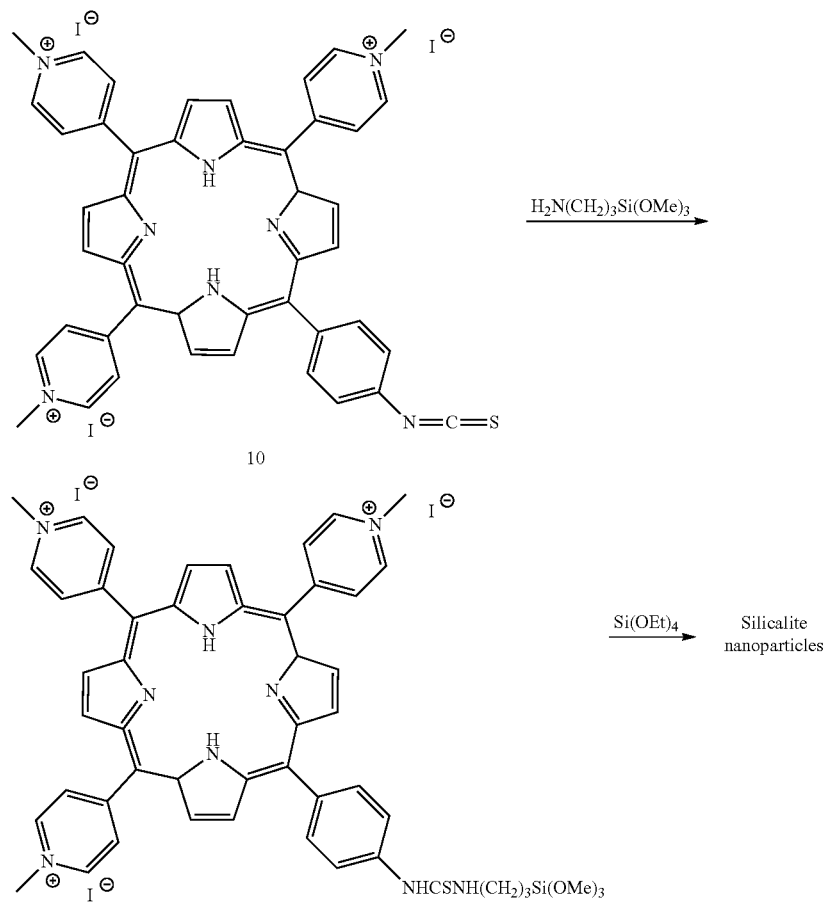

4.9 mg of the porphyrin 10 are dissolved in 1 ml of absolute EtOH with ultrasound. 2 µl of aminopropyltriethoxysilane are added and the reaction is maintained at ambient temperature overnight. The preceding reaction is dissolved, with vigorous stirring, with 14 ml of 1M tetrapropylammonium hydroxide in water, 8.4 ml of tetraethoxysilane and 2 ml of H$_2$O, in a polyethylene flask. The solution is stirred for 24 h at ambient temperature and is then placed in an oven at 80° C. without stirring. After two days, the reaction is cooled and then centrifuged. The nanoparticles are redispersed in water with ultrasound, and then centrifuged (3 cycles). The structuring agent is extracted with an EtOH/12N HCl (4/1) solution for 2 h at 60° C. Two cycles are carried out. The nanoparticles are then washed with H$_2$O 6 times (6 cycles:

dispersion in water with ultrasound-centrifugation) until a pH of 3.5 is obtained. The nanoparticles are then washed twice with EtOH.

X-ray diffraction: structured network
DLS: 92 nm
BET: 100 m²/g.

E—Synthesis of Mesoporous Nanoparticles Encapsulating a Cationic Porphyrin

OH21 Nanoparticles are added. The solution is kept stirring for 6 minutes and then rapidly neutralized to pH 7 by adding 0.2 M HCl (approximately 25 ml). The nanoparticles are recovered by centrifugation (20 minutes at 20 000 rpm), resuspended in EtOH with ultrasound, and centrifuged. The surfactant is extracted by treatment with 15 ml of EtOH/12N HCl (4/1) solution for 2 h at 60° C. After centrifugation, the operation is repeated twice, and then the nanoparticles are resuspended in water and centrifuged until a pH of about 6 is obtained (6 times).

IR analysis confirms the elimination of, the surfactant.

TEM shows the presence of a hexagonal network of mesopores with a nanoparticle diameter of about 150 nm.

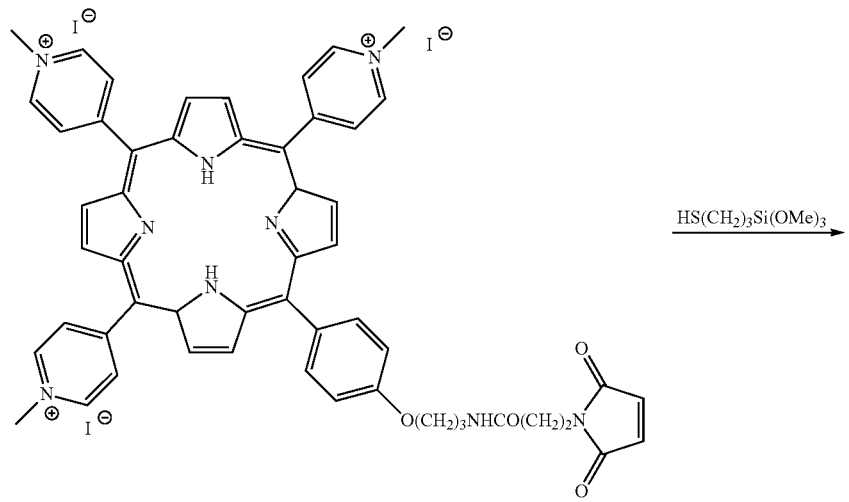

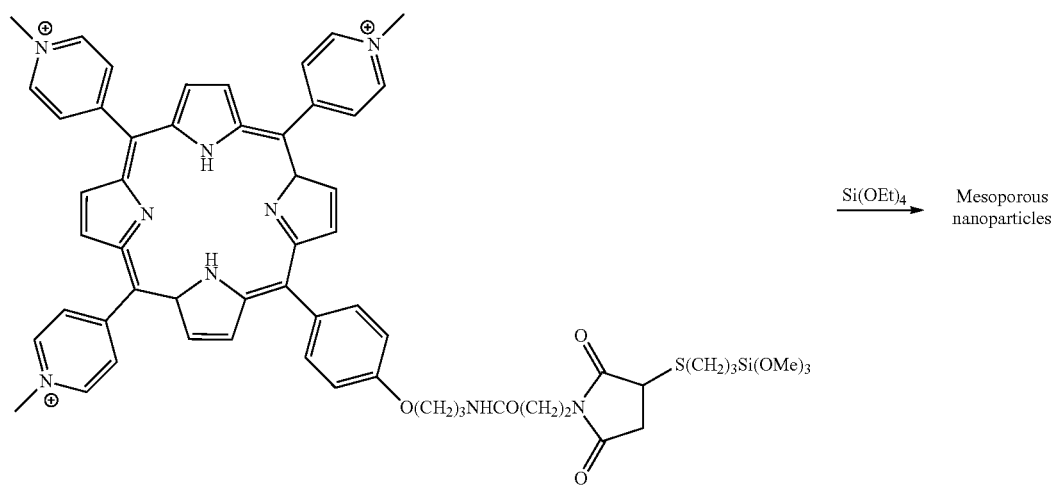

8 mg of the porphyrin 8 (6.3×10⁻³ mmol) are dissolved in 1 ml of MeOH. 4.2 mg of mercaptopropyltrimethoxysilane (21.78×10⁻³ mmol) are added and the reaction is maintained at ambient temperature overnight. 343 mg (0.9×10⁻³ mol) of cetyltrimethylammonium bromide (CTAB) are dissolved in 20 ml of 0.2M sodium hydroxide at 25° C. The solution previously prepared is added, as is tetraethoxysilane (1.75 ml, 0.8×10⁻² mmol). After 40 seconds, 128 ml of deionized water DLS shows a hydrodynamic diameter of 311 nm.

UV analysis (EtOH) confirms the presence of the covalently encapsulated porphyrin. A load of 4.43 μmol of porphyrin per g of nanoparticles is obtained.

The ability of the nanoparticles to generate singlet oxygen is evaluated by phosphorescence thereof after irradiation in one of the absorption bands of the photosensitizer, and in particular at 431 nm, of 3 mg of nanoparticles in 5 ml of absolute EtOH. The quantum yield for singlet oxygen formation is 58%.

F—Synthesis of Mesoporous Nanoparticles Encapsulating a Cationic Porphyrin

OH 22 Particles

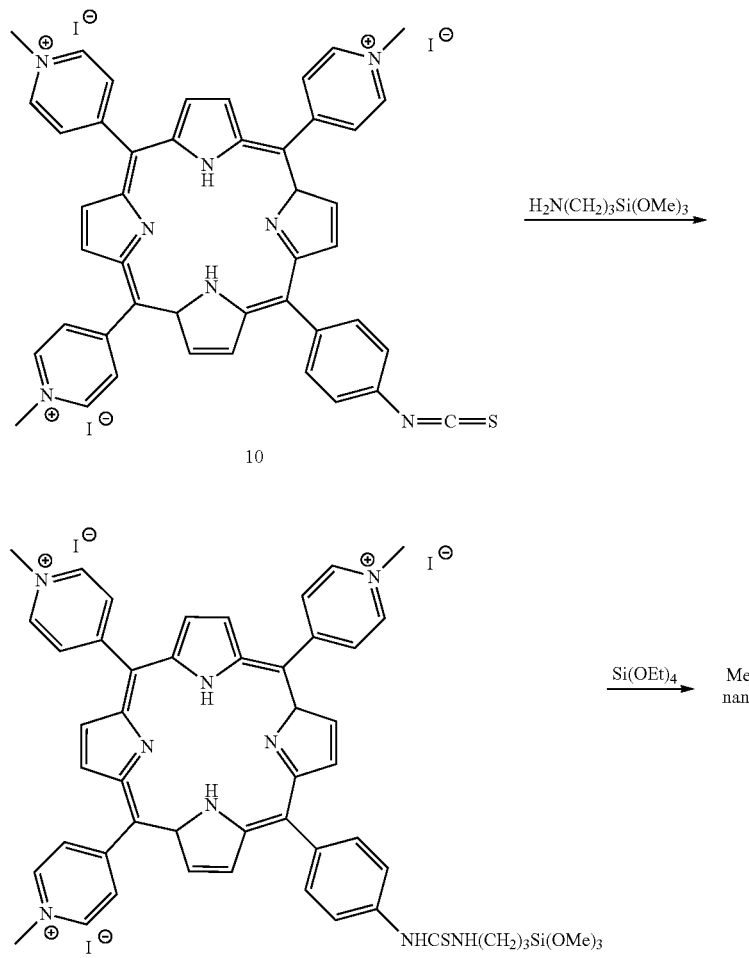

10

12 mg of the porphyrin 10 (1.1×10⁻² mmol) are dissolved in 1 ml of MeOH. 4.88 mg of aminopropyltrimethoxysilane (2.72×10⁻² mmol) are added and the solution is maintained at ambient temperature overnight. 343 mg (0.9×10⁻³ mol) of cetyltrimethylammonium bromide (CTAB) are dissolved in 20 ml of 0.2M sodium hydroxide at 25° C. Tetraethoxysilane (1.75 ml, 0.8×10⁻² mmol) is added dropwise, as is the solution previously prepared. After 40 seconds, 128 ml of deionized water are added. The solution is kept stirring for 6 minutes and then rapidly neutralized to pH 7 by adding 0.2 M HCl (approximately 25 ml). The nanoparticles are recovered by centrifugation (20 minutes at 20 000 rpm), resuspended in EtOH with ultrasound, and centrifuged. The surfactant is extracted by treatment with 15 ml of EtOH/12N HCl (4/1) solution for 2 h at 60° C. After centrifugation, the operation is repeated twice, and then the nanoparticles are resuspended in water and centrifuged until a pH of about 6 is obtained (6 times).

IR analysis confirms the elimination of the surfactant.

TEM (FIG. 2) shows the presence of a hexagonal network of mesopores with a nanoparticle diameter of about 150 nm.

DLS confirms the hydrodynamic diameter of 153 nm.

UV analysis (EtOH) confirms the presence of the covalently encapsulated porphyrin. A load of 0.97 µmol of porphyrin per g of nanoparticles is obtained.

The ability of the nanoparticles to generate singlet oxygen is evaluated by phosphorescence thereof after irradiation in one of the absorption bands of the photosensitizer, and in particular at 431 nm, of 3 mg of nanoparticles in 5 ml of absolute EtOH. The quantum yield for singlet oxygen formation is 60%.

G—Grafting of α-Mannose at the Surface of the Nanoparticles

DB016 Particles

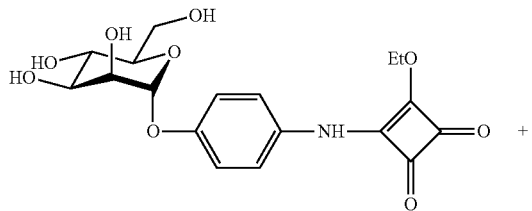

-continued

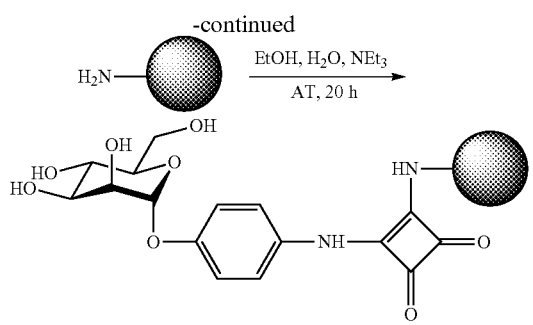

100 mg of aminated DB 015 nanoparticles prepared in §B above are dispersed with ultrasound for 10 minutes in 5 ml of EtOH. 59 mg (0.15 mmol) of α-mannose aryl squarate are dissolved in 5 ml of an EtOH/H$_2$O mixture (50/50). The solution is added dropwise to the above. 500 µl of triethylamine are added and the suspension is stirred for 18 h. After centrifugation, the nanoparticles are redispersed in water and centrifuged (3 cycles). They are then redispersed in EtOH and centrifuged (two cycles).

DLS analysis indicates a hydrodynamic diameter of 173 nm.

UV analysis confirms the presence of the porphyrin and of the aromatic nucleus-squarate (FIG. 3).

DB 021 Nanoparticles

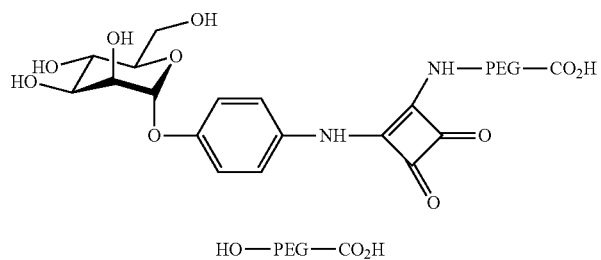

250 mg ($7.35 \times 10^{-5}$ mol) of H$_2$N-PEG-CO$_2$H (molar mass 3400) are dissolved in 1.25 ml of distilled water. Two equivalents (0.0148 mol) of triethylamine are added. 81 mg (2.5 equivalents) of phenylsquarate-mannose are dissolved in 1 ml of water. This solution is added dropwise to the previous solution. The reaction is maintained at ambient temperature for 15 h. The DMF is evaporated off and then the PEG is crystallized from ether, which is evaporated off.

66 mg ($2 \times 10^{-5}$ mol) of previous product and 256 mg ($9 \times 10^{-5}$ mol) of HO$_2$C-PEG-OH are dissolved in 10 ml of DMF. 21 µl of Et$_3$N, 15 mg of NHS (N-hydroxysuccinimide) and 30 mg of DCC (dicyclohexylcarbodiimide) are added. The reaction is maintained at ambient temperature overnight, and then 200 mg of DB 019 nanoparticles are added. After 20 h, the solution is centrifuged, the nanoparticles are resuspended in DMF with ultrasound, and then the solution is centrifuged again. The washing with DMF is repeated once, and then the nanoparticles are washed three times with water and twice with EtOH.

178 mg of DB 021 nanoparticles are obtained.

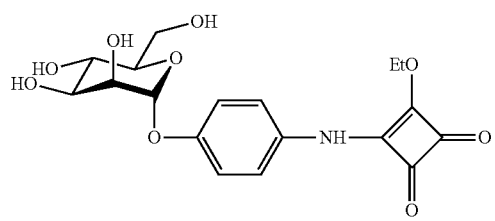

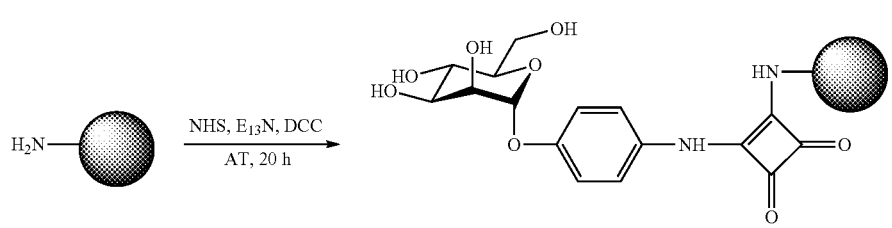

H—Grafting of α-Mannose-6-Carboxylate at the Surface of the Nanoparticles

DB 054 Particles

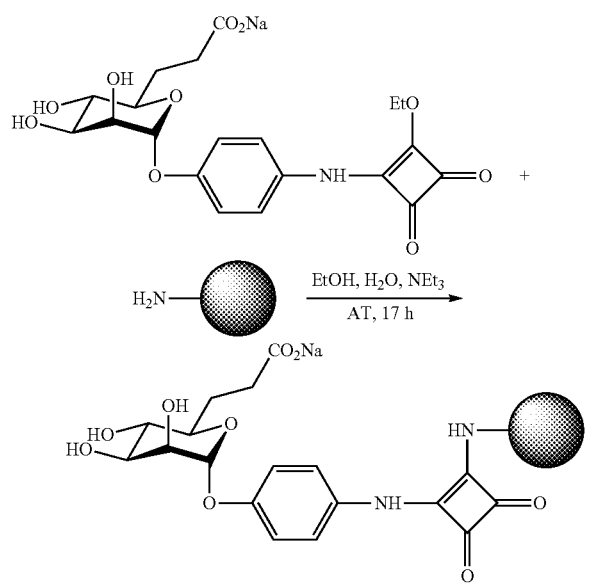

56 mg of DB 015 aminated nanoparticles are redispersed with ultrasound for 10 minutes in 5 ml of EtOH. 25 mg (0.055 mmol) of α-mannose-6-carboxylate squarate are dissolved in 5 ml of an EtOH/H$_2$O mixture (3/2). The solution is added dropwise to the above. 400 μl of triethylamine are added and the suspension is stirred for 17 h. After centrifugation, the nanoparticles are redispersed in water and centrifuged (3 cycles) and then redispersed in EtOH and centrifuged (three cycles).

33 mg of DB 054 nanoparticles are obtained.

III—BIOLOGICAL ACTIVITY

The activities in photodynamic therapy (PDT) of the various nanoparticles which are nonfunctionalized or functionalized with a biomolecule are evaluated in various cell lines. The cytotoxic efficacy of the nanoparticles internalized in cancer cells is tested after single-photon excitation of the encapsulated porphyrins. The efficacy of the PDT is shown by the relative innocuousness of the nonirradiated particles. The specificity of the targeting and of the endocytosis of the nanoparticles is shown by coincubation of the functionalized nanoparticle and of the corresponding biomolecule.

Example 1

Figure 6:
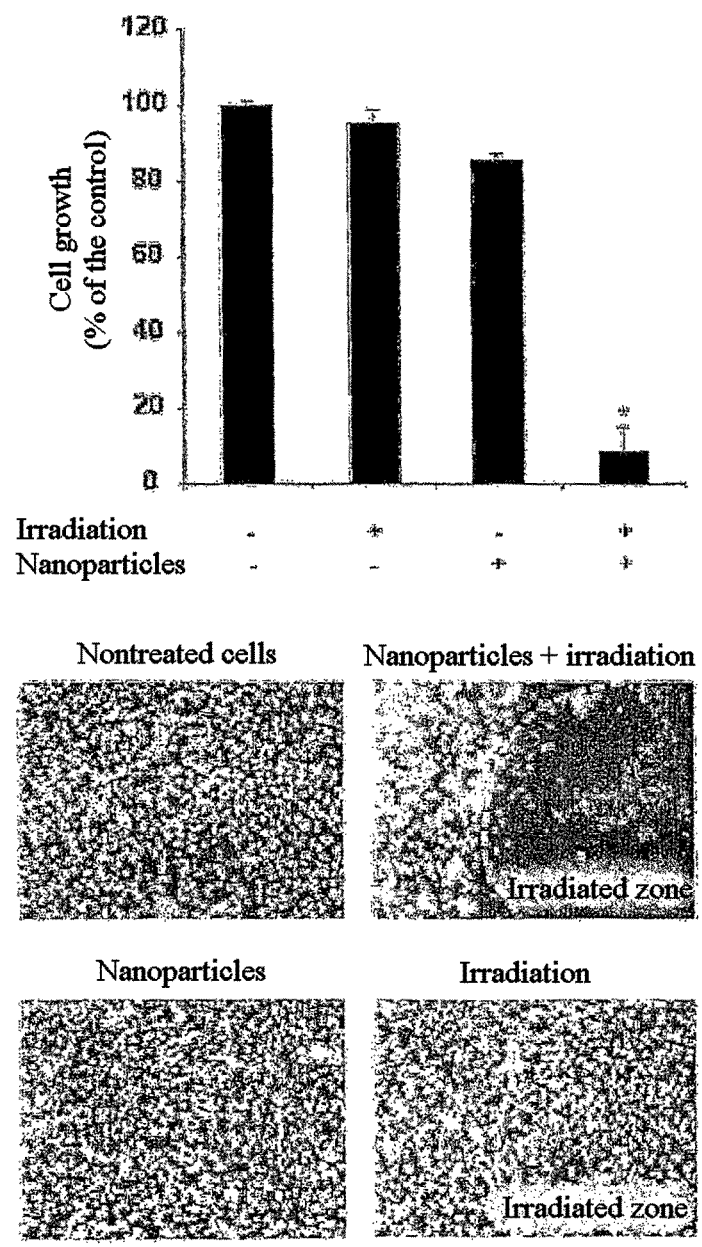

PDT Activity of the OH21 Nanoparticles on MDA-MB-231 Breast Cancer Cells (FIG. 6)

Experimental Conditions:
MDA-MB-231 breast cancer cells, maintained in culture in Dulbecco's modified Eagle's medium supplemented with 10% of FCS, in a humid atmosphere at 37° C. and 5% CO$_2$, are seeded into 96-well plates at a density of 30 000 cells per well, in 100 μl of medium. The MDA-MB-231 breast cancer cells, which have the ability to perform phagocytosis, are incubated for 24 h with 20 μg/ml of nanoparticles and irradiated for 40 min with a laser at 650 nm (power 2 to 10 mW/cm$^2$). Two days after the irradiation, the live cells are quantified using the MTT (3-(4,5-dimethyl-thiazol-2-yl)-2,5-diphenyltetrazolium bromide, Sigma) enzymatic assay.

Results:

the efficacy of the photodynamic therapy is reflected by a 92% inhibition of cell growth. The absence of toxicity of the nonirradiated nanoparticles and the absence of toxicity of the irradiation in the absence of nanoparticles demonstrate the specificity of the photodynamic therapy with these nanoparticles. The cells are visualized by fluorescent labeling of the nuclei with DAPI. The images obtained show the specificity of the photodynamic therapy using the nanoparticles of the invention. Cell death is obvious and exclusively in the zone irradiated and in the presence of nanoparticles.

Example 2

Figure 7:
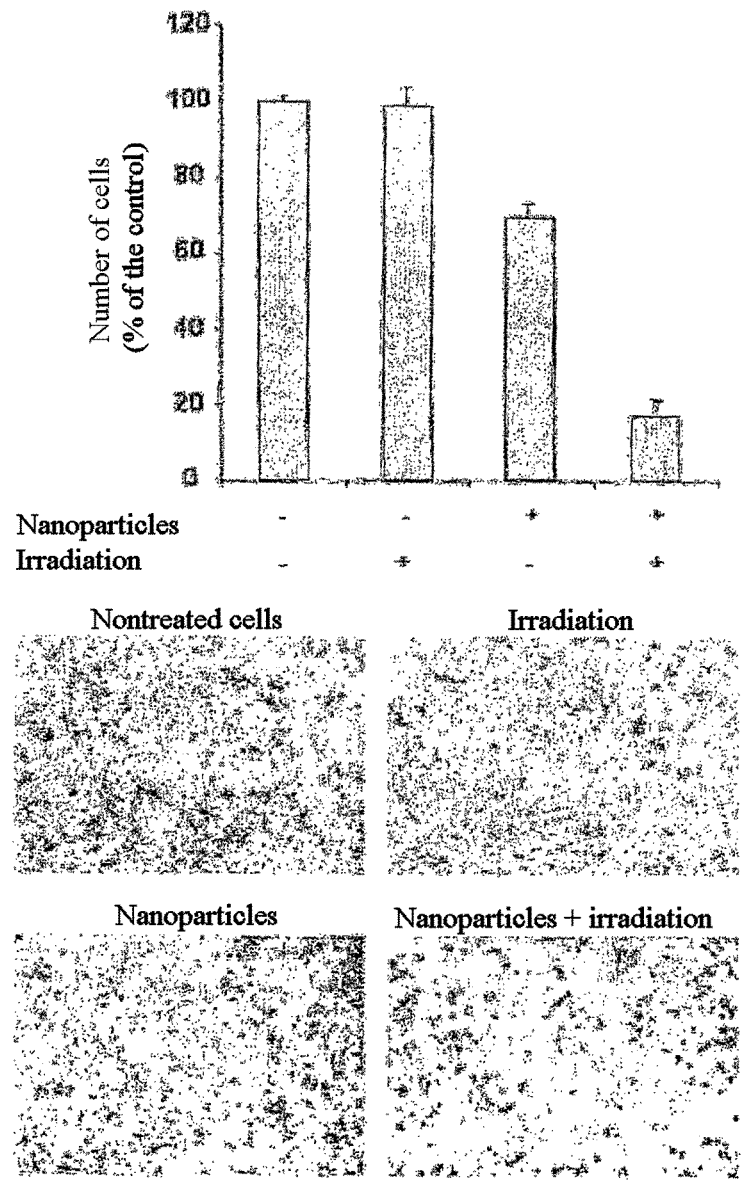

PDT Activity of the OH21 Nanoparticles on POE14 Ovarian Cancer Cells (FIG. 7)

Experimental Conditions:

POE14 cells are maintained in culture as described in example 1, incubated for 24 h with a nanoparticle concentration reduced to 10 μg/ml and irradiated as described in example 1. Two days after irradiation, the addition of MTT to the medium makes it possible to quantify the number of live cells.

Results:

the irradiation of the nanoparticles incubated with the POE14 cells induces a cell death of 82% compared with the control cells or cells only irradiated. In this cell type, the nonirradiated nanoparticles induce a decrease in the number of live cells of approximately 30%. This toxicity demonstrates the need for specific targeting.

Example 3

Figure 8:
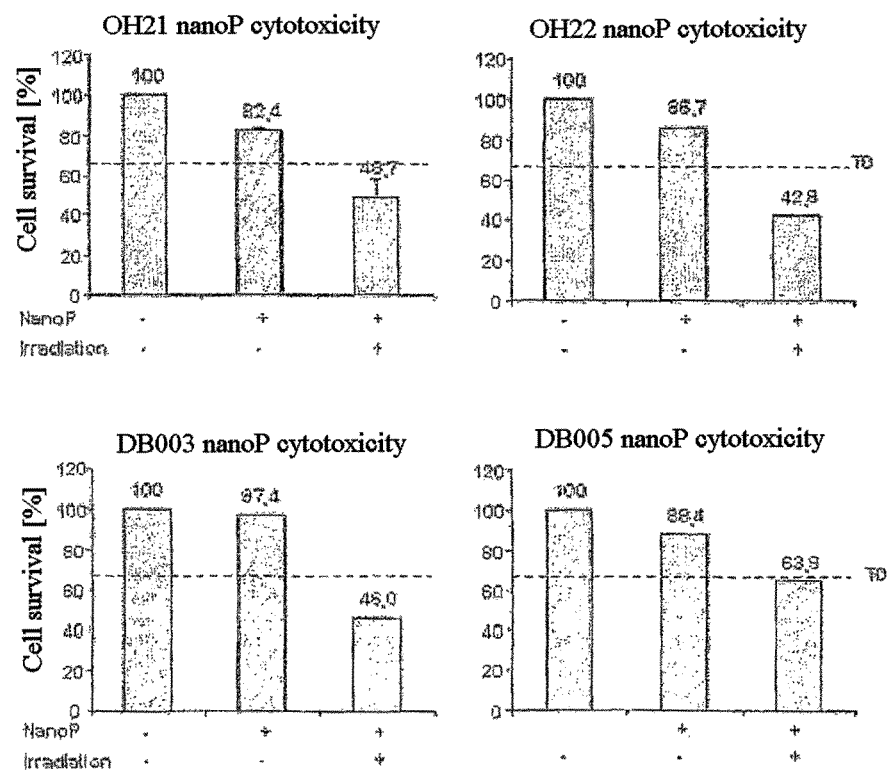

PDT Activity of the OH21 and OH22 Cationic Nanoparticles and DB003 and DB005 Anionic Particles on MDA-MB-231 Breast Cancer Cells (FIG. 8)

Experimental Conditions:

identical to example 1.

Results:

The results obtained make it possible to compare the efficacy of the nanoparticles containing either anionic porphyrins or cationic porphyrins. FIG. 8 shows that all the irradiated nanoparticles tested completely inhibit the growth of MDA-MB-231 cells, compared with the T0 value which corresponds to the initial cell seeding before irradiation. In addition, the irradiation of the OH21 and OH22 nanoparticles, which contain cationic porphyrins, induces a cell death of 51.3% and 57.2%, respectively, compared with the control (nontreated cells). The DB003 and DB005 nanoparticles containing anionic porphyrins induce, after irradiation, a cell death of 37.1% and 54%, respectively. The cytotoxicity (low but significant) of certain nonirradiated nanoparticles demonstrates the advantages of specific targeting coming from mannose.

Example 4

Figure 9:
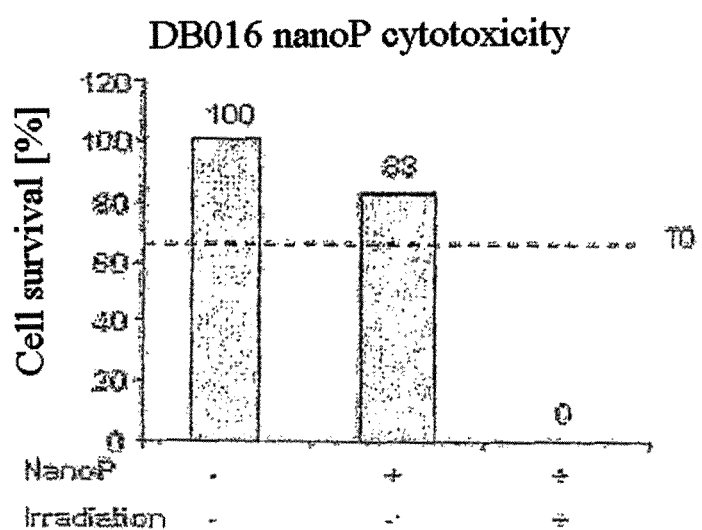
Figure 9:
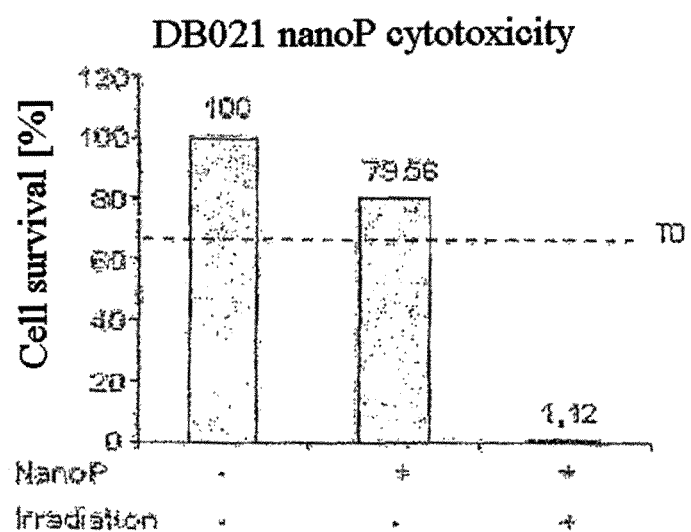

PDT Activity of the Mannose-Functionalized Anionic Nanoparticles on MDA-MB-231 Breast Cancer Cells (FIG. 9)

Experimental Conditions:
identical to example 1.
Results:
The results obtained make it possible to compare the efficacy of the nanoparticles containing anionic porphyrins, which are uncoated or coated with mannose. The DB016 and DB021 nanoparticles at the surface of which mannose residues have been grafted, induce a cell death of 100% and 99%, respectively. These results demonstrate the increase in cytotoxic efficacy of the nanoparticles owing to the targeting that comes from the mannose.

Example 5

Figure 10:
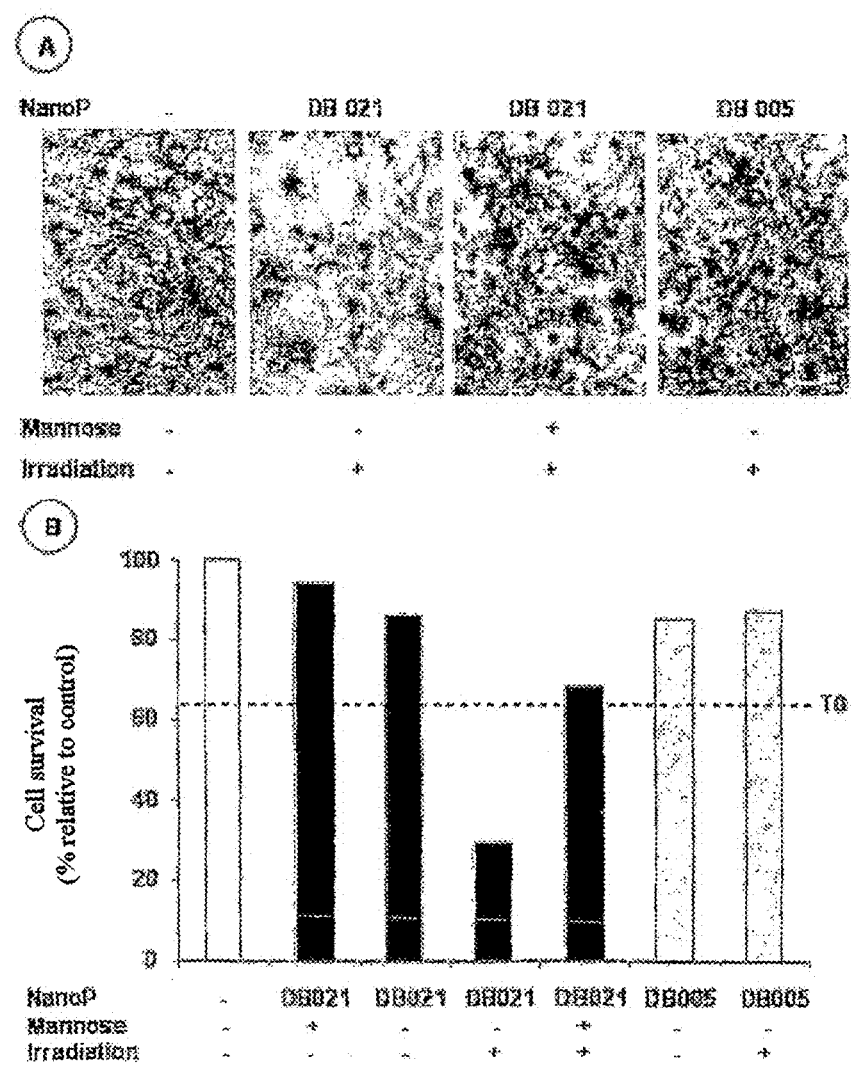

Comparison of the PDT Activities of the Mannose-Functionalized or Nonfunctionalized Anionic Nanoparticles on MDA-MB-231 Breast Cancer Cells in the Presence or Absence of an Excess of Mannose (FIG. 10)

Experimental Conditions:
The cells are incubated for 6 hours in medium optionally supplemented with mannose ($10^{-2}$ M), in the presence or absence of 20 μg/ml of nanoparticles (DB021 or DB005). After 6 h of incubation, the nanoparticles in the medium are removed and the cells are rinsed twice and then cultured in 100 μl of fresh medium. The cells are then subjected to laser irradiation at a wavelength of 630-680 nm, with a power of 2 to 10 mW/cm$^2$, for 40 min. 48 h after irradiation, the live cells are revealed (A) and quantified (B) by MTT.
Results:
FIG. 10A shows the control level of MTT accumulation in the nontreated cells. Incubation of the cells with the DB021 nanoparticles subjected to irradiation results in cell death. This phenomenon is blocked by preincubation with an excess of mannose. The irradiated DB005 nanoparticles do not induce cell death. The quantification of the live cells (FIG. 10B) confirms these observations. The cytotoxicity due to the DB021 nanoparticles incubated for 6 h is only 2 to 10% (±mannose), whereas irradiation of the DB021 nanoparticles induces 70% cell death. The addition of an excess of mannose stops this effect to a large extent, thereby demonstrating the specificity of the internalization. Furthermore, the irradiated or nonirradiated DB005 nanoparticles induce only 5 to 10% cell death.

Example 6

Figure 11:
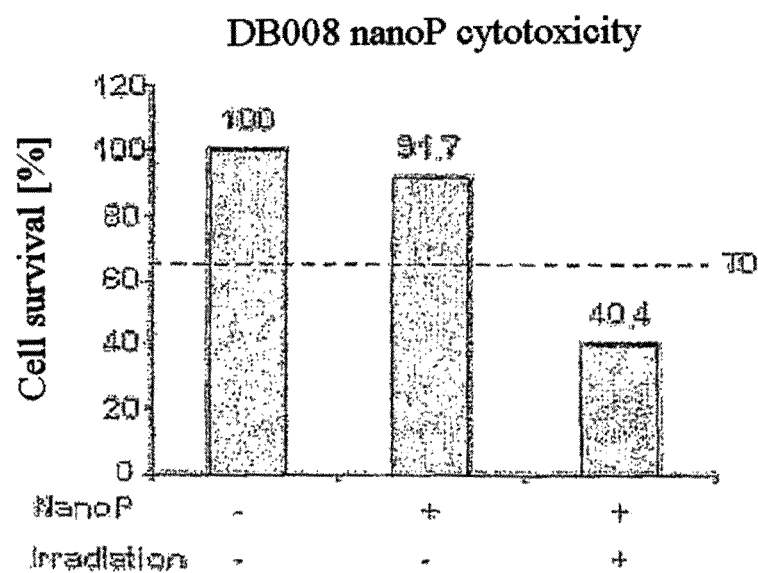
Figure 11:
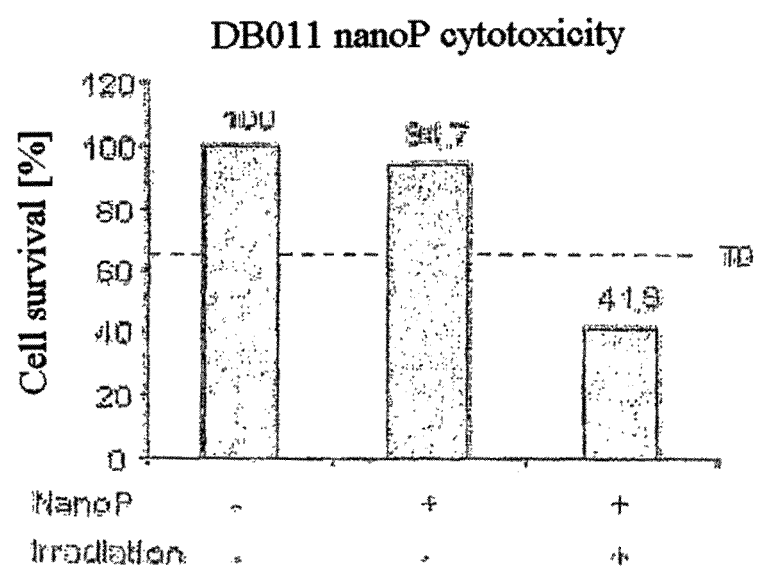

PDT Activity of the DB008 and DB011 Silicalite Nanoparticles on MDA-MB-231 Breast Cancer Cells (FIG. 11)

Experimental Conditions:
identical to example 1.
Results:
The results obtained show that the DB008 and DB011 silicalite nanoparticles exhibit a low toxicity of 8.3% and 5.3% when they are not irradiated. Irradiation of the cells incubated with these nanoparticles (for 24 h) induces total inhibition of growth and a cell death of approximately 60%.

Example 7

Figure 12:
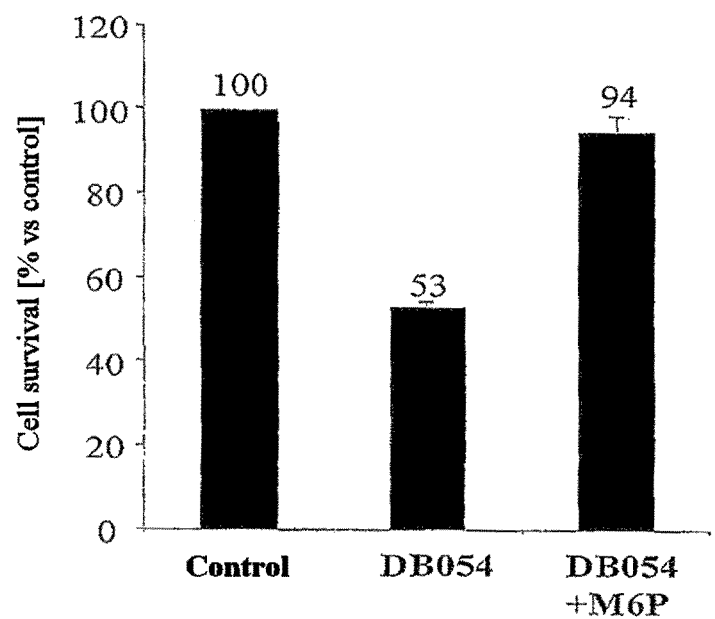

PDT Activity of the DB054 Nanoparticles on LNCaP Prostate Cancer Cells: Specificity of DB054 Internalization (FIG. 12)

Experimental Conditions:
Human prostate cancer cells (LNCaP) are incubated for 1 h with the DB054 nanoparticles in a serum-free medium at 37° C., in the presence or absence of an excess of M6P, and then subjected to laser irradiation (660 nm, 6-7 mW/cm$^2$, 40 min). The percentage of live cells is determined using the MTS test (Promega). The graphic representations correspond to the mean of 3 independent experiments.
Results:
The results obtained show that the D5054 nanoparticles induce a cell death of 47% after one hour of treatment. This effect is blocked by the addition to the medium of an excess of 10 mM M6P, which demonstrates internalization of the DB054 nanoparticles via the membrane receptor for M6P.

Example 8

Figure 13:
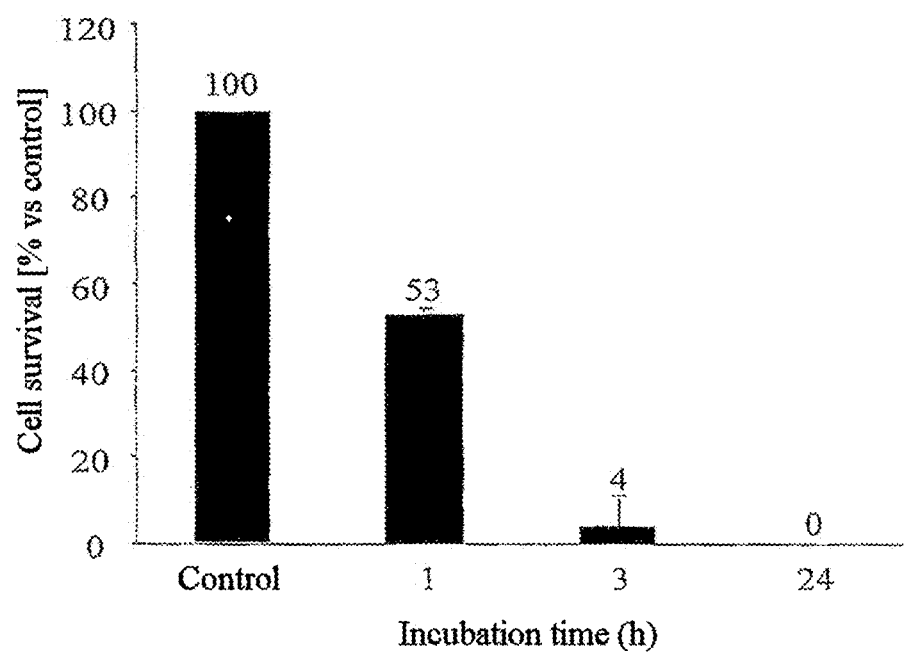

PDT Activity of the DB054 Nanoparticles on LNCaP Prostate Cancer Cells: Variation in Efficacy Over Time of DB054 (FIG. 13)

Experimental Conditions:
Human prostate cancer cells (LNCaP) are incubated for different periods of time (1 h, 3 h, 24 h) with the DB054 nanoparticles and then subjected to laser irradiation (660 nm, 6-7 mW/cm$^2$, 40 min). The percentage of live cells is determined using the MTS test (Promega). The graphic representations correspond to the mean of 3 independent experiments.
Results:
The results obtained show that the DB054 nanoparticles induce, respectively, 47%, 96% and 100% cyttotoxicity after 1 h, 3 h and 24 h of treatment. These results demonstrate the rapid action of the nanoparticles.

Example 9

Figure 14:
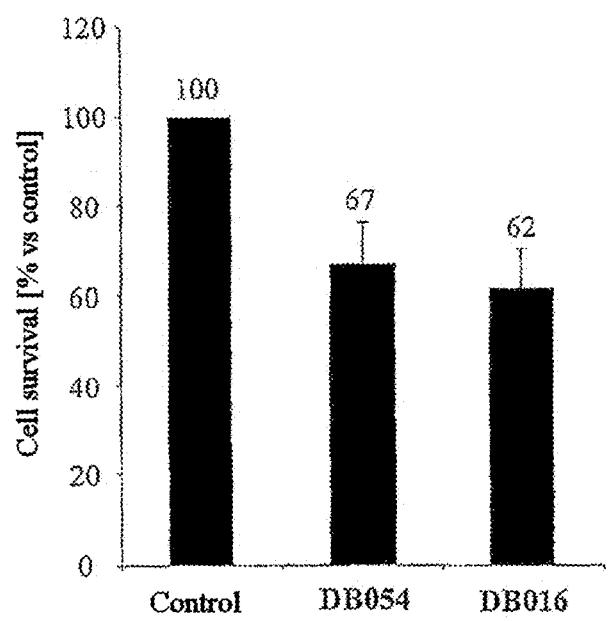

PDT Activity of the DB016 and DB054 Nanoparticles on Human Retinoblastoma Cells (FIG. 14)

Experimental Conditions:
Human retinoblastoma cells (Y-79) are incubated for 1 h with the DB054 and DB016 nanoparticles in a complete medium at 37° C., and then subjected to laser irradiation (660 nm, 6-7 mW/cm$^2$, 40 min). The percentage of live cells is determined using the MTS test (Promega). The graphic representations correspond to the mean of 3 independent experiments.
Results:
The results obtained show that the DB054 and DB016 nanoparticles induce, respectively, 33% and 38% cell cytotoxicity. This demonstrates that the nanoparticles functionalized with mannose-6-phosphate or with mannose can be efficiently internalized via various lectins present at the surface of the Y-79 cells.

The invention claimed is:

1. A molecule corresponding to formula (I) below:

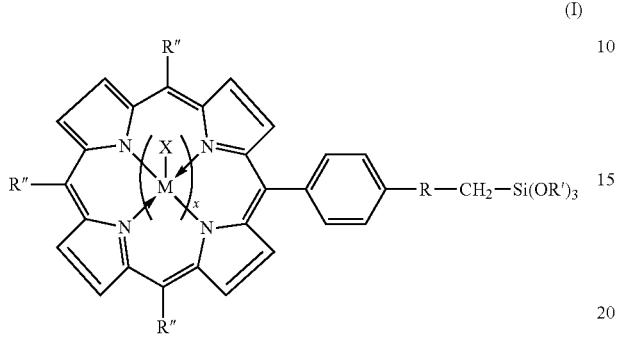

in which:

x represents an integer chosen from: 0 and 1,

M represents a metal atom chosen from transition metals, when X represents 0, (M-X) is replaced with two hydrogen atoms, X represents a group chosen from: a halide, and an anion of a carboxylic acid which is pharmaceutically acceptable, R represents a group chosen from:
a $C_1$-$C_{15}$ alkyl chain, optionally interrupted with one or more groups chosen from: an ether (—O—), an amine (—NH—), a thioether (—S—), a ketone (—CO—), an ester (—CO—O—), an amide (—CO—NH—), a urea (—NH—CO—NH—), a thiourea (—NH—CS—NH—), an oxycarbonyl (—O—CO—O—) and a carbamate (—NH—CO—O—), R' represents a group chosen from: a $C_1$-$C_6$ alkyl, a phenyl and a benzyl, R" represents a group chosen from:

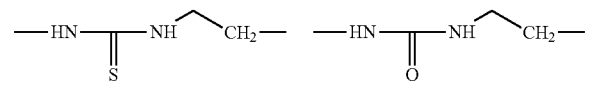

and $Z^+$ represents a pharmaceutically acceptable organic or inorganic cation, $Y^-$ represents a group which may be chosen from: —COO$^-$ and —SO$_3^-$, $A^-$ represents an anion which may be chosen from: a halide, and an anion of a carboxylic acid which is pharmaceutically acceptable, $R^1$ represents a $C_1$ to $C_{10}$ alkyl.

2. The molecule as claimed in claim 1, in which

M represents a metal atom chosen from: Zn, Pt, Pd, Mn, Gd, Ni, Cr and Ru,

X represents a group chosen from: Cl$^-$, Br$^-$, I$^-$, acetate, propionate, butyrate, ascorbate, benzoate, cinnamate, citrate, fumarate, glycolate, malonate, tartrate, malate, maleate, mandelate and tosylate, R represents a group chosen from:
a $C_1$-$C_{10}$ alkyl chain, optionally interrupted with one or more groups chosen from: an ether (—O—), an amine (—NH—), a thioether (—S—), a ketone (—CO—), an ester (—CO—O—), an amide (—CO—NH—), a urea (—NH—CO—NH—), a thiourea (—NH—CS—NH—), an oxycarbonyl (—O—CO—O—) and a carbamate (—NH—CO—O—), R' represents a group chosen from: a $C_1$-$C_3$ alkyl, $R^1$ represents a group chosen from: a $C_1$-$C_3$ alkyl, $Z^+$ represents a cation which may be chosen from: K$^+$, Li$^+$, Na$^+$ and NH$_4^+$, $A^-$ represents an anion which may be chosen from: Cl$^-$, Br$^-$, I$^-$, acetate, propionate, butyrate, ascorbate, benzoate, cinnamate, citrate, fumarate, glycolate, malonate, tartrate, malate, maleate, mandelate and tosylate.

3. The molecule as claimed in claim 2, in which:

X represents a group chosen from: Cl$^-$, Br$^-$, I$^-$, acetate and tosylate,

R is chosen from:

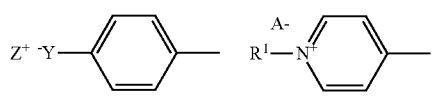

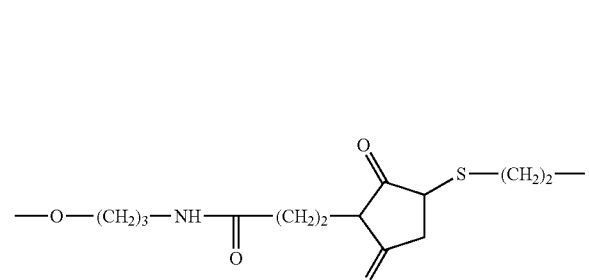

R' represents a group chosen from: a methyl and an ethyl, $R^1$ represents a methyl, $A^-$ represents an anion which may be chosen from: Cl$^-$, Br$^-$, I$^-$, acetate and tosylate.

4. The molecule as claimed in claim 1, which is chosen from:
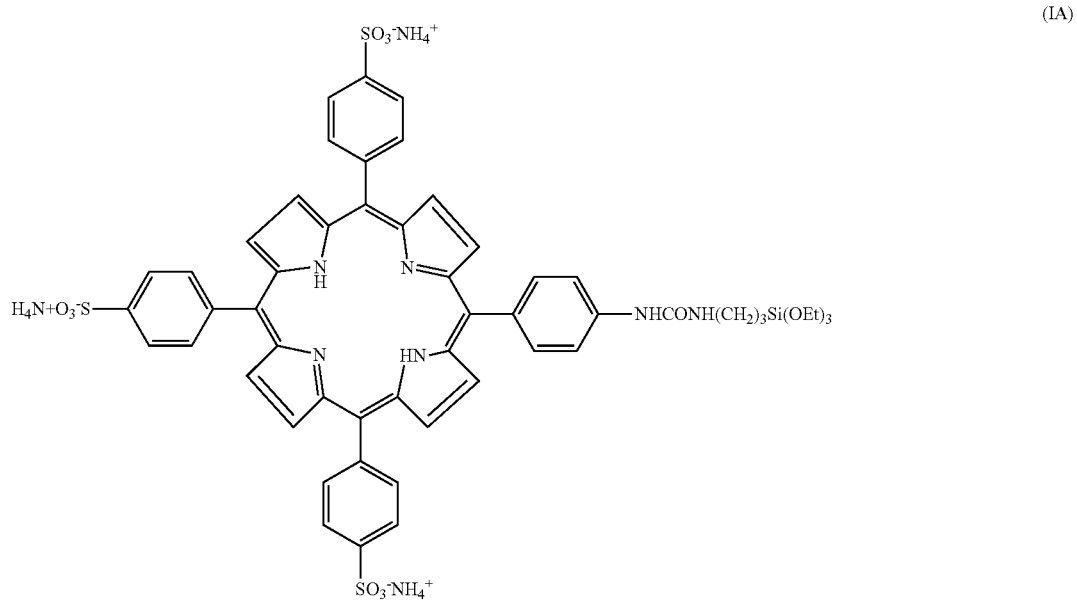
(IA)
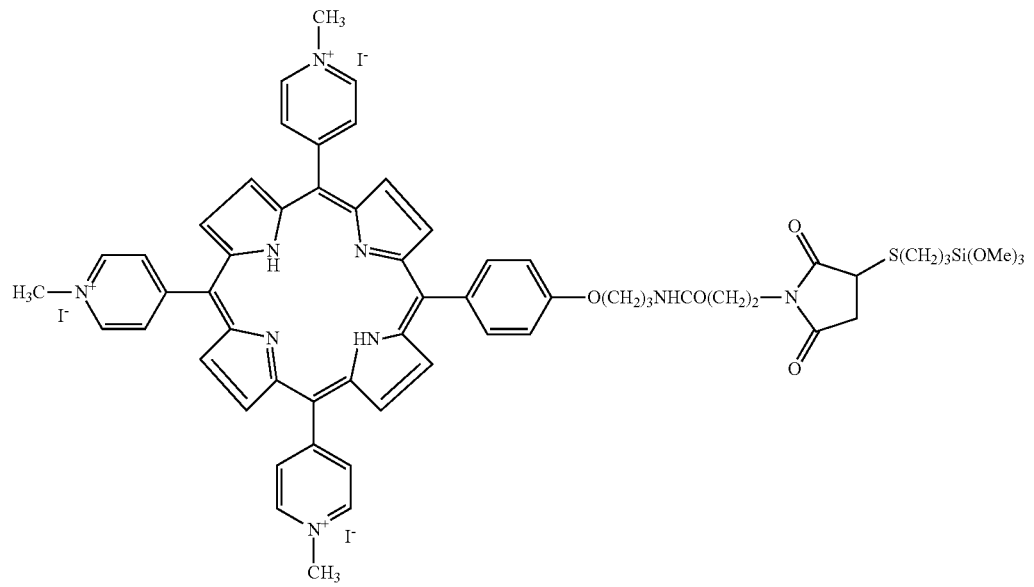
(IB)

-continued

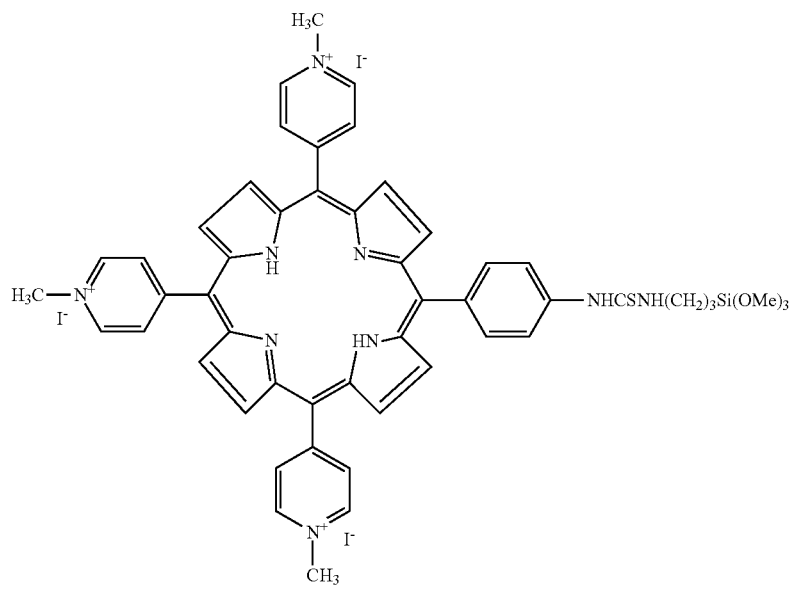

(IC)

5. A composition of silica-based nanoparticles comprising at least one photosensitizer corresponding to formula (I) as claimed in claim 1.

6. The composition as claimed in claim 5, in which the nanoparticles have an organized porosity.

7. The composition as claimed in claim 6, in which the silica nanoparticles are mesoporous.

8. The composition as claimed in claim 7, in which the mesoporous silica nanoparticles have a particle size ranging from 80 to 400 nm in diameter, a specific surface area ranging from 800 to 1000 m$^2$/g and pore sizes ranging from 2 to 6 nm.

9. The composition as claimed in claim 6, in which the silica nanoparticles are microporous.

10. The composition as claimed in claim 9, in which the nanoparticles have a diameter of between 40 and 80 nm, a specific surface area ranging from 100 to 450 m$^2$/g and pore diameters ranging from 2 to 20 Å.

11. The composition as claimed in claim 5, which comprises grafting on the surface of the nanoparticles with targeting molecules specific for neoplastic tissues.

12. The composition as claimed in claim 11, in which the targeting molecule is chosen from derivatives of sugar, in particular mannose.

* * * * *